United States Patent [19]

Livesey et al.

[11] Patent Number: 5,336,616
[45] Date of Patent: Aug. 9, 1994

[54] METHOD FOR PROCESSING AND PRESERVING COLLAGEN-BASED TISSUES FOR TRANSPLANTATION

[75] Inventors: Stephen A. Livesey, Eltham, Australia; Anthony A. del Campo; Abhijit Nag, both of Houston, Tex.; Ken B. Nichols, The Woodlands, Tex.; Christopher Coleman, Houston, Tex.

[73] Assignee: LifeCell Corporation, The Woodlands, Tex.

[21] Appl. No.: 4,752

[22] Filed: Feb. 2, 1993

Related U.S. Application Data

[63] Continuation-in-part of Ser. No. 835,138, Feb. 12, 1992, abandoned, which is a continuation-in-part of Ser. No. 709,504, Jun. 3, 1991, abandoned, which is a continuation-in-part of Ser. No. 581,584, Sep. 12, 1990, abandoned.

[51] Int. Cl.$^5$ ............... C12N 5/00; A01N 1/02; A61F 2/10
[52] U.S. Cl. ................ 435/240.2; 435/1; 623/15
[58] Field of Search ........... 435/1, 240.2, 240.3; 62/62; 623/15

[56] References Cited

U.S. PATENT DOCUMENTS

| | | | |
|---|---|---|---|
| 3,228,838 | 1/1966 | Rinfret et al. | 167/74 |
| 3,649,163 | 3/1972 | McCusker | 8/94.11 |
| 4,205,132 | 5/1980 | Sandine et al. | 435/260 |
| 4,229,544 | 10/1980 | Haynes et al. | 435/253 |
| 4,323,358 | 4/1982 | Lentz et al. | 8/94.11 |
| 4,329,787 | 5/1982 | Newton | 34/1 |
| 4,352,887 | 10/1982 | Reid et al. | 435/240 |
| 4,383,832 | 5/1983 | Fraefel et al. | 8/94.11 |
| 4,559,298 | 12/1985 | Fahy | 435/1 |
| 4,567,847 | 2/1986 | Linner | 118/50.1 |
| 4,688,387 | 8/1987 | Conaway | 62/78 |
| 4,707,998 | 11/1987 | Linner et al. | 62/349 |
| 4,776,853 | 10/1988 | Klement et al. | 8/94.11 |
| 4,799,361 | 1/1989 | Linner | 62/64 |
| 4,801,299 | 1/1989 | Brendel et al. | 623/1 |
| 4,807,442 | 2/1989 | Linner et al. | 62/55.5 |
| 4,865,871 | 9/1989 | Livesey et al. | 427/4 |
| 4,874,690 | 10/1989 | Goodrich, Jr. | 435/2 |
| 4,964,280 | 10/1990 | Piunno et al. | 62/78 |
| 4,980,277 | 12/1990 | Junnila | 435/2 |
| 5,024,830 | 6/1991 | Linner | 424/3 |
| 5,045,446 | 9/1991 | Goodrich, Jr. | 435/2 |
| 5,131,850 | 7/1992 | Brockbank | 435/1 |
| 5,145,770 | 9/1992 | Tubo et al. | 435/1 |
| 5,153,004 | 10/1992 | Goodrich, Jr. | 424/533 |
| 5,171,661 | 12/1992 | Goodrich, Jr. | 435/2 |
| 5,178,884 | 1/1993 | Goodrich, Jr. | 424/533 |

FOREIGN PATENT DOCUMENTS

| | | |
|---|---|---|
| 0267026 | 5/1988 | European Pat. Off. |
| 1522286 | 3/1968 | France |
| 2104349 | 3/1972 | France |
| WO91/18504 | 12/1291 | PCT Int'l Appl. |
| 614532 | 11/1979 | Switzerland |
| 0997640 | 2/1983 | U.S.S.R. |
| 351132 | 7/1931 | United Kingdom |
| 1482785 | 8/1977 | United Kingdom |

OTHER PUBLICATIONS

E. Mayer, "New Method for Vitrifying Water and Other Liquids by Rapid Cooling of Their Aerosols" Journal of Applied Physics, vol. 58, No. 2, pp. 663–667.

Brendel et al., Vascular Basement Membranes: Preparation and Properites of Material Isolated with the Use of (List continued on next page.)

Primary Examiner—Irene Marx
Assistant Examiner—Susan M. Dadio
Attorney, Agent, or Firm—Arnold, White & Durkee

[57] ABSTRACT

A method for processing and preserving an acellular collagen-based tissue matrix for transplantation is disclosed. The method includes the steps of processing biological tissues with a stabilizing solution to reduce procurement damage, treatment with a processing solution to remove cells, treatment with a cryoprotectant solution followed by freezing, drying, storage and rehydration under conditions that preclude functionally significant damage and reconstitution with viable cells.

4 Claims, No Drawings

OTHER PUBLICATIONS

Detergents, *Advances in Experimental Medicine and Biology*, vol. 131, pp. 89–103, New York (1980).

Carlson et al., Ultrastructural and Biochemical Analysis of Isolated Basement Membranes from Kidney Glomeruli and Tubules and Brain and Retinal Microvessels, *J. Ultrastruct. Res.* 62, pp. 26–53 (1978).

Duhamel et al, Morphology of Bovine Cerebral and Retinal Microvascular Basement Membranes and Electrophoretic Characterization of Differential Extracts, *Bibl. Anat.* 20, pp. 134–137 (1980).

Meezan et al., A Versatile Method for the Isolation of Ultrastructurally and Chemically Pure Basement Membranes Without Sonication, *Biology and Chemistry of Basement Membranes*, pp. 17–30, New York (1978).

Meezan et al, Structural and Functional Properties of Acellular, Histoarchitecturally Intact Basement Membranes, *Frontiers of Matrix Biology*, vol. 7, pp. 110–119 (1979).

Meezan et al., A Simple, Versatile Non-Disruptive Model for the Isolation of Porphologically and Chemically Pure Basement Membranes from Several Tissues, *Life Sci.* 17, pp. 1721–1732 (1975).

Brendel et al., The Acellular Prefused Kidney: A Model for Basement Membrane Permeability, *Biology and Chemistry of Basement Membranes*, pp. 177–193, New York (1978).

Kuttan et al, Preparation and Composition of Aveolar Extracellular Matrix and Incorporated Basement Membrane, *Lung* 159, pp. 333–345 (1981).

Duhamel et al., Selective Solubilization of Two Populations of Polypeptides from Bovine Retinal Basement Membranes, *Exp. Eye Res.* 36, pp. 257–267 (1983).

Lafranconi et al., Rapid Isolation of Type II Pneumocytes with Magnetic Removal of Macrophages, *Experimental Lung Research* 4, pp. 191–204 (1983).

Ohno et al., Isolation and Characterization of Human Placental Chorionic Villar Extracellular Matrix, *Journal of Supramolecular Structure* 12, pp. 457–466 (1979).

Ohno et al., Human Placental Chorionic Villar Extracellular Matrix. 2. Solubilization and Characterization from Villar Fragments Fractionated According to Their Size, *Biological Research in Pregnancy* vol. 1, No. 2, pp. 79–89 (1980).

Ohno et al., Human Placental Chorionic Villar Extracellular Matrix 1. Preparation and Chemical Composition from Villar Fragments Fractionated According to Their Size, *International Journal of Biological Research in Pregnancy*, vol. 1, No. 1, pp. 38–47.

Johnson et al., Preparation of Cell-Free Extracellular Matrix From Human Peripheral Nerve, *Muscle and Nerve* 5, pp. 335–344 (1982).

Spall et al., Rat Hepatocytes in Suspension Culture and on Basement Membrane Substrate, (Paper 1978).

Diani et al., Physiological and Pathological Relevance of Fatty Acids in Amniotic Fluid, *Biological Research in Pregnancy*, vol. 1, No. 2, pp. 90–94 (1980).

Meryman, H. T., Absence of Unfrozen Freezable Water in Rapidly Frozen Red Cells, *Cryobiology*, vol. 7, pp. 252–255 (1971).

Terracio, L. and Schwabe, K. G., Freezing and Drying of Biological Tissues for Electron Microscopy, *Journal of Histochemistry and Cytochemistry*, vol. 29, No. 9, pp. 1021–1028 (1981).

Coulter, H. D. et al., Preparation of Biological Tissues for Electron Microscopy by Freeze-Drying, *Anatomical Record*, vol. 187, No. 4, pp. 477–493 (1977).

Escaig, Jacques, New Instruments Which Facilitate Rapid Freezing at 83K and 6K, *Journal of Microscopy*, vol. 126, Pt. 3, pp. 221–222 (1982).

Boyne, Alan F., A Gentle, Bounce-Free Assembly for Quick-Freezing Tissues for Electron Microscopy: Application to Isolated Torpedine Ray Electrocyte Stacks, *Journal of Neuroscience Methods*, vol. 1, pp. 353–364 (1979).

Coulter, H. David, Freezing and Drying of Biological Tissues With a Toggle-Link Helium Freezer and an Improved Freeze-Drying Apparatus: Application to Neuropeptide Immunocytochemistry, *Journal of Electron Microscopy Technique*, vol. 4, pp. 315–328 (1986).

Reichert-Jung, Cryovacublock–*Instruction Manual.*

Escaig, Jacques, Control of Different Parameters for Optimal Freezing Conditions, *Science of Biological Specimen Preparation*, pp. 117–122.

Handley et al., The Design and Use of a Simple Device for Rapid Quench-Freezing of Biological Samples, *Journal of Microscopy*, vol. 121, Pt. 3, pp. 273–282 (1981).

(List continued on next page.)

OTHER PUBLICATIONS

Polaron Instruments, Inc., The Slammer, (Brochure); Med-Vac, Inc., Cryopress, (Brochure).
Reichert-Jung, Cryofract 190 Cryoblock, (Brochure).
Quick Freezing Devices, *Quick Freezing by Bounce--Free Delivery* (Brochure).
Moor, et al., The Influence of High Pressure Freezing on Mammalian Nerve Tissue, *Cell and Tissue Research*, vol. 209, pp. 201-216 (1980).
Langdon et al., Reconstitution of Structure and Cell Function in Human Skin Grafts Derived From Cryopreserved Allogeneic Dermis and Autologous Cultured Keratinocytes, *Journal of Investigative Dermatology*, vol. 91, No. 5, pp. 478-485 (1988).
May et al., *Journal of MAG*, vol. 73, pp. 233-236 (1984).
Lejeune, B. et al., Betterave rough: réalisation d'atomisats et de lyophilisats, *Annales Pharmaceutiques Francaises*, Tomme 44, No. 6, pp. 461-466 (1986).
Athreya, Balu H. et al., "Differential Susceptiblity of Epithelial Cells and Fibroblasts of Human Skin to Freeze Injury", *Cryobiology*, vol. 5, No. 4, 1969, pp. 262-269.
Chambler, K. et al., "The Use of Etox Lyophilised Skin in Burns", *British Journal Plastic Surgery*, 22(3), Jul. 1969, pp. 210-215.
Batchelor, J. R. et al., "HL-A Matching in Treatment of Burned Patients with Skin Allografts", *The Lancet*, Sep. 19, 1970, pp. 581-583.
Abbott, William M. et al., "Absence of Antigenicity in Freeze-Dried Skin Allografts", *Cryobiology*, vol. 6, No. 5, 1970, pp. 416-418.
Bondoc, C. C. et al., "Clinical Experience with Viable Frozen Human Skin and A Frozen Skin Bank", *Ann. Surg.* vol. 174, No. 3, 1971, pp. 371-382.
Graham, William P. III et al., "Versatility of Skin Allografts: Desirability of a Viable Frozen Tissue Bank", *The Journal of Trauma*, vol. 11, No. 6, 1971, pp. 494-501.
Burke, John F. et al., "Temporary Skin Transplantation and Immunosuppression for Extensive Burns", *The New England Journal of Medicine*, vol. 290, No. 5, Jan. 31, 1974, pp. 269-271.
Reddi, A. H. et al., "Bone Matrix in The Solid State Geometric Influence on Differentiation of Fibroblasts", *Medical Physics*, vol. 15 X+310p., 1974, pp. 1-17.

McGregor, John C. et al., "The Behaviour of Cialit-Stored and Freez-Dried Human Fascia Lata in Rats", *British Journal of Plastic Surgery*, (27), 1974, pp. 155-164.
Reddi, A. H. et al., "Formation of Bone Marrow in Fibroblast-Transformation Ossicles", *Proc. Nat. Acad. Sci. USA*, vol. 72, No. 6, Jun. 1975, pp. 2212-2216.
Helenius, Ari et al., "Solubilization of Membranes by Detergents", *Biochimica et Biophysica Acta* 415, 1975, pp. 29-79.
DeLoecker, W. et al., "Metabolic Changes in Rat Skin During Preservation and Storage in Glycerol Buffer at $-196°$ C.", *Cryobiology* 13, (1976), pp. 24-30.
Nathan, P. et al., "Burn Wounds: Selection and Preservation of Skin, Natural Products, Blood, and Blood Products for Burn Therapy", *CRC Critical Reviews in Clinical Laboratory Sciences*, May 1976, pp. 1-31.
Friedlaender, Gary E. et al., "Studies on the Antigenicity of Bone", *The Journal of Bone and Joint Surgery* 58(6), Sep. 1976, pp. 854-858.
Ninnemann, J. L. et al., "Clinical Skin Banking: A Simplified System for Processing, Storage, and Retrieval of Human Allografts", Third Denver Postgraduate Institute in Emergency Medicine, Oct. 1978.
Wachtel, Thomas L. et al., "Viability of Frozen Allografts", *The American Journal of Surgery*, vol. 138, Dec. 1979, pp. 783-787.
Prows, Janalyn et al., "Evaluation of Storage Conditions for Refrigerated Rabbit Skin", *Cryobiology* 17, (1980), pp. 125-129.
DeLoecker, W. et al., "Metabolic Changes in Human Skin Preserved at $-3$ and at $-196°$ C.", *Cryobiology* 17, (1980), pp. 46-53.
Weiss, Roy E. et al., "Appearance of Fibronectin During the Differentiation of Cartilage, Bone, and Bone Marrow", *The Journal of Cell Biology*, vol. 88, Mar. 1981, pp. 630-636.
Goldman, Mitchell H. et al., "Lyophilized Veins as Arterial Interposition Allografts", *Cryobiology*, 18, (1981) pp. 306-312.
Carter, William G., "Transformation-dependent Alterations in Glycoproteins of the Extracellular Matrix of Human Fibroblasts", *The Journal of Biological Chemistry*, vol. 257, No. 22, Nov. 25, 1982, pp. 13805-13815.
Sampath, T. K. et al., "Homology of Bone-Inductive (List continued on next page.)

OTHER PUBLICATIONS

Proteins from Human, Monkey, Bovine, and Rat Extracellular Matrix", *Cell Biology*, vol. 80, Nov. 1983, pp. 6591–6595.

Pruniéras, Michel et al., "Methods for Cultivation of Keratinocytes with an Air–Liquid Interface", *The Journal of Investigative Dermatology*, vol. 81, No. 1, 1983, pp. 28s–33s.

Lichtenberg, Dov et al., "Solubilization of Phospholipids by Detergents", *Biochimica et Biophysica Acta* 737 (1983) pp. 285–304.

Pruitt, Baisl A. Jr. et al., "Characteristics and Uses of Biologic Dressings and Skins Substitutes", *Arch Surg* vol. 119, Mar. 1984, pp. 312–322.

Swaim, Steven F., "Skin Grafts", *Veterinary Clinics of North America: Small Animal Practice*, vol. 20, No. 1, Jan. 1990, pp. 147–175.

Kearney, J. N. et al., "Cryopreservation of Skin Using a Murine Model: Validation of a Prognostic Viability Assay", *Cryobiology* 27, (1990), pp. 24–30.

Konstantinow, Alexander et al., "Skin Banking: A Simple Method for Cryopreservation of Split–Thickness Skin and Cultured Human Epidermal Keratinocytes", *Annals of Plastic Surgery*, vol. 21, No. 1, Jan. 1991, pp. 89–97.

Cinamon, Udi et al., "A Simplified Testing System to Evaluate Performance After Transplantation of Human Skin Preserved in Glycerol or in Liquid Nitrogen", *Journal of Burn Care & Rehabilitation*, Jul./Aug. 1993, vol. 14, No. 4, pp. 435–439.

Hyatt, G. W. et al., "New Methods for Preserving Bone, Skin and Blood Vessels".

Barlyn, Lyle W. et al., "Frozen Skin Autografts Protected by Dimethyl Sulfoxide", *Surgical Forum Plastic Surgery*, pp. 475–477.

Marrangoni, Albert G., "An Experimental Study on Refrigerated Skin Grafts Stored in Ten Per Cent Homologous Serum", pp. 425–434.

Cram, Alert E. et al., "Short-term Preservation of Human Autografts", *The Journal of Trauma*, vol. 23, No. 10, pp. 872–873.

METHOD FOR PROCESSING AND PRESERVING COLLAGEN-BASED TISSUES FOR TRANSPLANTATION

RELATED APPLICATION

This application is a continuation-in-part of copending application Ser. No. 07/835,138, filed Feb. 12, 1992, now abandoned, which is a continuation-in-part of copending application Ser. No. 07/709,504, filed Jun. 3, 1991, now abandoned, which is a continuation-in-part of copending application Ser. No. 07/581,584, filed Sep. 12, 1990, now abandoned.

BACKGROUND OF THE INVENTION

1. Field of the Invention

This invention relates to methods for procuring decellularizing and further processing and dry preserving collagen-based tissues derived from humans and animals for transplantation into humans or other animals. These methods produce a tissue product that consists of a selectively preserved extracellular protein matrix that is devoid of certain viable cells which normally express major histocompatibility complex antigenic determinants and other antigens which would be recognized as foreign by the recipient. This extracellular protein matrix is made up of collagen and other proteins and provides a structural template which may be repopulated with new viable cells that would not be rejected by the host. These viable cells may be derived from the host (autologous cells) before or after transplantation or from an alternative human source including foreskin, umbilical cord or aborted fetal tissues. More particularly, this invention relates to the procurement and processing of collagen-based tissues such that complications following implantation (including but not limited to immunorejection, contracture, calcification, occlusion, and infection) are significantly reduced relative to current implant procedures and materials.

2. Description of the Related Art

Tissue and organ transplantation is a rapidly growing therapeutic field as a result of improvements in surgical procedures, advancements in immunosuppressive drugs and increased knowledge of graft/host interaction. Despite major advancements in this field, modern tissue transplantation remains associated with complications including inflammation, degradation, scarring, contracture, calcification (hardening), occlusion and rejection. There are numerous investigations underway directed toward the engineering of improved transplantable tissue grafts, however, it is generally believed in the industry that ideal implants have yet to be produced.

Autologous or self-derived human tissue is often used for transplant procedures. These procedures include coronary and peripheral vascular bypass surgeries, where a blood vessel, usually a vein, is harvested from some other area of the body and transplanted to correct obstructed blood flow through one or more critical arteries. Another application of autologous tissue is in the treatment of third degree burns and other full-thickness skin injury. This treatment involves grafting of healthy skin from uninjured body sites to the site of the wound, a process called split-skin grafting. Additional applications of autologous tissue transplantation include bone, cartilage and fascia grafting, used for reconstructive procedures.

The motive for using autologous tissue for transplantation is based upon the concept that complications of immunorejection will be eliminated, resulting in enhanced conditions for graft survival. Unfortunately, however, other complications can ensue with autologous transplants. For example, significant damage can occur to several tissue components of transplanted veins during harvesting and prior to implantation. This damage can include mechanical contraction of the smooth muscle cells in the vein wall leading to loss of endothelium and smooth muscle cell hypoxia and death. Hypoxic damage can result in the release of cellular lysosomes, enzymes which can cause significant damage to the extracellular matrix. Following implantation, such damage can lead to increased platelet adhesion, leucocyte and macrophage infiltration and subsequently further damage to the vessel wall. The end result of such damage is thrombosis and occlusion in the early post implant period. Even in the absence of such damage, transplanted autologous veins typically undergo thickening of the vessel wall and advancing atherosclerosis leading to late occlusion. The exact cause of this phenomena is uncertain but may relate to compliance mismatch of the vein in an arterial position of high blood pressure and flow rate. This phenomena may be augmented and accelerated by any initial smooth muscle cell and matrix damage occurring during procurement. Occlusion of transplanted veins can necessitate repeat bypass procedures, with subsequent re-harvesting of additional autologous veins, or replacement with synthetic conduits or non-autologous vessels.

Another example of complications resulting from autologous tissue transplantation is the scarring and contracture that can occur with split-skin grafts for full-thickness wound repair. Split-skin grafts are typically mechanically expanded by the use of a meshing instrument, which introduces a pattern of small slits in the skin. The split-skin graft is then stretched to cover a larger wound area. Dividing epidermal cells will ultimately grow into and cover the areas of the slits, however, the underlying dermal support matrix does not readily expand into these areas. The dermal matrix, composed primarily of collagen, other extracellular protein matrix proteins, and basement membrane complex, is responsible for the tensile, flexible nature of skin. Absence of a dermal matrix results in scarring and contracture in the area of the slits. This contracture can be severe and in cases of massively burned patients that undergo extensive split-skin grafting, can necessitate subsequent release surgical procedures to restore joint movement.

When the supply of transplantable autologous tissues is depleted, or when there is no suitable autologous tissue available for transplant (e.g., heart valve replacement), then substitutes may be used, including man-made synthetic materials, animal-derived tissues and tissue products, or allogeneic human tissues donated from another individual (usually derived from cadavers). Man-made implant materials include synthetic polymers (e.g. (PTFE) polytetrafluroethylene, Dacron and Goretex) sometimes formed into a tubular shape and used as a blood flow conduit for some peripheral arterial bypass procedures. Additionally, man-made synthetics (polyurethanes) and hydrocolloids or gels may be used as temporary wound dressings prior to split-skin grafting.

Other man-made materials include plastics and carbonized metals, fashioned into a prosthetic heart valve, utilized for aortic heart valve replacement procedures.

Synthetic materials can be made with low immunogenicity but are subject to other limitations. In the case of mechanical heart valves, their hemodynamic characteristics necessitate life-long anticoagulant therapy. Synthetic vascular conduits, often used in above-the-knee peripheral vascular bypass procedures, are subjected to an even higher incidence of occlusion than autologous grafts. In many cases, a preference is made for a biological implant which can be a processed animal tissue or a fresh or cryopreserved allogeneic human tissue.

Animal tissues (bovine or porcine) chemically treated are commonly used as replacements for defective human heart valves, and have been used in the past for vascular conduits. The concept in the chemical processing is to stabilize the structural protein and collagen matrix by cross-linking with glutaraldehyde or a similar cross-linking agent. This treatment also masks the antigenic determinants, such that the human host will not recognize the implant as foreign and precludes an immunorejection response. Glutaraldehyde-treated tissues, however, will not allow in-migration of host cells which are necessary for remodeling, and will gradually harden as a result of calcification. For this reason, glutaraldehyde-treated tissues generally require replacement in 5–7 years. Glutaraldehyde-treated bovine veins have been used in the past for vascular bypass bypass procedures, however, their use has been discontinued due to the unacceptable incidence of aneurysm formation and occlusion.

The use of allogeneic transplant tissues has been applied to heart valve replacement procedures, arterial bypass procedures, bone, cartilage, and ligament replacement procedures and to full-thickness wound treatment as a temporary dressing. The allogeneic tissue is used fresh, or may be cryopreserved with the use of DMSO and/or glycerol, to maintain viability of cellular components. It is thought that the cellular components contain histocompatibility antigens, and are capable of eliciting an immune response from the host. In many cases, the patient receiving the allogeneic transplant undergoes immunosuppressive therapy. Despite this therapy, many allogeneic transplants, including heart valves and blood vessels, undergo an inflammatory response, and fail within 5–10 years. Allogeneic skin is typically rejected within 1–5 weeks of application, and has never been demonstrated to be permanently accepted by the host, even with the use of immunosuppressive drugs.

Alternative processing methods have been developed by others that are intended to address the limitations of allogeneic and animal-derived transplant tissues. Freeze-drying is used routinely in the processing of allogeneic bone for transplantation. It has been found that the freeze drying process results in a graft which elicits no significant rejection response as compared to fresh or cryopreserved allogeneic bone. The freeze-dried bone following implant acts as a template, which is subsequently remodelled by the host. When the freeze-drying process has been applied to more complex tissues such as heart valves, the results have been mixed but overall unsatisfactory. A study was conducted in which 15 allogeneic heart valves were processed by freeze-drying prior to transplantation. Most of the freeze-dried valves failed due to mechanical causes in the early post-graft interval. Those freeze-dried valves which did not fail, however, demonstrated prolonged functionality (up to 15 years).

Enzymes and detergent processing has also been used to remove antigenic cells from collagen-based transplantable tissues. Organic solvents and detergent treatments have been used successfully with relatively simple tissues such as dura mater used in reconstructive surgical procedures. Chemical processing of more complex structures such as heart valves, vascular conduits and skin, however, has had only limited success in clinical applications.

The invention of this patent is a comprehensive processing technique that addresses potential damaging events in the preparation of complex collagen-based tissues for transplantation. The technology combines both biochemical and physical processing steps to achieve the ideal features of template function such that the tissue graft can be remodeled for long-term maintenance by the host.

BRIEF SUMMARY OF THE INVENTION

In its preferred form, the method of this invention includes the steps of processing biological tissues including treatment with a stabilizing solution to reduce procurement damage, treatment with a processing solution to remove cells and other antigenic tissue components, treatment with a cryoprotectant solution, freezing and storage under specific conditions to avoid functionally significant damaging ice crystal formation, drying under conditions to prevent damaging ice recrystallization, storage in the dry state at above freezing temperatures, rehydration under specific conditions and with a rehydration solution to minimize surface tension damage and farther augment the selective preservation of the matrix, and reconstitution with viable cells that will not be rejected by the host.

DESCRIPTION OF THE PREFERRED EMBODIMENTS

The present invention provides a method for processing and preserving collagen-based biological tissues for transplantation, through steps of chemical pretreatment and cell removal, cryopreparation, dry stabilization, drying, rehydration and cellular reconstitution. The processing and preservation method is designed to generate a transplantable biological tissue graft that specifically meets the following criteria:

(a) provides an extracellular protein and collagen matrix which can be remodelled and repaired by the host, (b) provides an intact basement membrane for secure reattachment of viable endothelial or epithelial cells, (c) does not elicit an immune response by the host, (d) does not calcify, and (e) can be easily stored and transported at ambient temperatures.

In the preferred embodiment, the biological tissue to be processed is first procured or harvested from a human cadaver or animal donor and immediately placed in a stabilizing transportation solution which arrests and prevents osmotic, hypoxic, autolytic and proteolytic degradation, protects against bacterial contamination and reduces mechanical damage that can occur with tissues that contain smooth muscle components (e.g. blood vessels). The stabilizing solution generally contains an appropriate buffer, one or more antioxidants, one or more oncotic agents, an antibiotic, one or more protease inhibitors, and in some cases, a smooth muscle relaxant.

In the preferred embodiment, the tissue is then incubated in a processing solution to remove viable antigenic cells (including epithelial cells, endothelial cells, smooth muscle cells and fibroblasts) from the structural matrix without damaging the basement membrane complex or the structural integrity of the collagen matrix. The processing solution generally contains an appropriate buffer, salt, an antibiotic, one or more detergents, one or more protease inhibitors, and/or one or more enzymes. Treatment of the tissue with this processing solution must be at a concentration for a time duration such that degradation of the basement membrane complex is avoided and the structural integrity of the matrix is maintained including collagen fibers and elastin.

After the tissue is decellularized, it is preferably incubated in a cryopreservation solution. In the preferred embodiment, this solution generally contains one or more cryoprotectants to minimize ice crystal damage to the structural matrix that could occur during freezing, and one or more dry-protective components, to minimize structural damage alteration during drying and may include a combination of an organic solvent and water which undergoes neither expansion or contraction during freezing. As an alternate method, the decellularized tissue matrix can be fixed with a crosslinking agent such as glutaraldehyde and stored prior to transplantation. Following incubation in this cryopreservation solution, the tissue is packaged inside a sterile container, such as a glass vial or a pouch, which is permeable to water vapor yet impermeable to bacteria.

In the preferred embodiment, one side of this pouch consists of medical grade porous Tyvek membrane, a trademarked product of DuPont Company of Wilmington, Del. This membrane is porous to water vapor and impervious to bacteria and dust. The Tyvek membrane is heat sealed to a 2.5 millimeter impermeable polythylene laminate sheet, leaving one side open, thus forming a two-sided pouch. The open pouch is sterilized by gamma radiation prior to use. The tissue is aseptically placed through this opening into the sterile pouch. The open side is then aseptically heat sealed to close the pouch. The packaged tissue is henceforth protected from microbial contamination throughout subsequent processing steps.

In the preferred embodiment, the packaged tissue is cooled to a low temperature at a specified rate which is compatible with the specific cryoprotectant to minimize damaging hexagonal ice and to generate the less stable ice forms of amorphous and cubic phases. The tissue is then dried at a low temperature under vacuum conditions, such that water vapor is removed sequentially from each ice crystal phase without ice recrystallization. Such drying is achieved either by conventional freeze drying or by using a previously patented molecular distillation dryer. Suitable molecular distillation dryers can be obtained from LifeCell Corporation in the Woodlands, Tex. and are disclosed in U.S. Pat. Nos. 4,567,847 and 4,799,361 which are incorporated herein by reference.

At the completion of the drying cycle of samples dried in a pouch, the vacuum of the freeze drying apparatus is reversed with a dry inert gas such as nitrogen, helium or argon. While being maintained in the same gaseous environment, the semipermeable pouch is placed inside an impervious pouch which is further heat or pressure sealed. The final configuration of the dry sample is therefore in an inert gaseous atmosphere, hermetically sealed in an impermeable pouch.

At the completion of the drying cycle of samples dried in a glass vial, the vial is sealed under vacuum with an appropriate inert stopper and the vacuum of the drying apparatus reversed with an inert gas prior to unloading.

In the preferred embodiment, the packaged dried tissue may be stored for extended time periods under ambient conditions. Transportation may be accomplished via standard carriers and under standard conditions relative to normal temperature exposure and delivery times.

In the preferred embodiment, the dried tissue is rehydrated prior to transplantation. It is important to minimize osmotic forces and surface tension effects during rehydration. The aim in rehydration is to augment the selective preservation of the extracellular support matrix while removing any residual antigenic cells and other potentially antigenic components. Appropriate rehydration may be accomplished by an initial incubation of the dried tissue in an environment of about 100% relative humidity, followed by immersion in a suitable rehydration solution. Alternatively, the dried tissue may be directly immersed in the rehydration solution without prior incubation in a high humidity environment. Rehydration should not cause osmotic damage to the sample. Vapor rehydration should ideally achieve a residual moisture level of at least 15% and fluid rehydration should result in a tissue moisture level of between 20% and 70%.

Depending on the tissue to be rehydrated, the rehydration solution may be simply normal saline, Ringer's lactate or a standard cell culture medium. Where the tissue is subject to the action of endogenous collagenases, elastases or residual autolytic activity from previously removed cells, additives to the rehydration solution are made and include protease inhibitors. Where residual free radical activity is present, agents to protect against hypoxia are used including antioxidants, enzymatic agents which protect against free radical damage and agents which minimize the disturbance of biochemical pathways which result from hypoxic damage. Antibiotics may also be included to inhibit bacterial contamination. Oncotic agents being in the form of proteoglycans, dextran and/or amino acids may also be included to prevent osmotic damage to the matrix during rehydration. Rehydration of a dry sample is especially suited to this process as it allows rapid and uniform distribution of the components of the rehydration solution. In addition, the rehydration solution may contain specific components not used previously, for example diphosphonates to inhibit alkaline phosphatase and prevent subsequent calcification. Agents may also be included in the rehydration solution to stimulate neovascularization and host cell infiltration following transplantation of the rehydrated extracellular matrix. Alternatively, rehydration may be performed in a solution containing a cross-linking agent such as glutaraldehyde.

Immunotolerable viable cells must be restored to the rehydrated structural matrix to produce a permanently accepted graft that may be remodeled by the host. In the preferred embodiment, immunotolerable viable cells may be reconstituted by in vitro cell culturing techniques prior to transplantation, or by in vivo repopulation following transplantation.

In the preferred embodiment the cell types used for in vitro reconstitution will depend on the nature of the transplantable graft. The primary requirement for reconstitution of full-thickness skin from processed and rehydrated dermis is the restoration of epidermal cells or keratinocytes. These cells may be derived from the intended recipient patient, in the form of a small meshed split-skin graft or as isolated keratinocytes expanded to sheets under cell culture conditions. Alternatively, allogeneic keratinocytes derived from foreskin or fetal origin, may be used to culture and reconstitute the epidermis.

The important cell for reconstitution of heart valves and vascular conduits is the endothelial cell, which lines the inner surface of the tissue. Endothelial cells may also be expanded in culture, and may be derived directly from the intended recipient patient or from umbilical arteries or veins.

Following drying, or following drying and rehydration, or following drying, rehydration and reconstitution, the processed tissue graft will be transported to the appropriate hospital or treatment facility. The choice of the final composition of the product will be dependent on the specific intended clinical application.

In the practice of this invention, it is fundamental that suitable tissues are obtained prior to processing. Human cadaver tissues are obtainable through approximately 100 tissue banks throughout the nation. Additionally, human tissues are obtainable directly from hospitals. A signed informed consent document is required from the donor's family to allow harvesting of tissues for transplantation. Animal tissues are obtainable from a number of meat processing companies and from suppliers of laboratory animals. The particular type of tissue harvested is not limiting on the method of this invention. However, processing of the tissue is enhanced by the use of specific procurement procedures, and treatment with a stabilizing solution to prevent certain mechanical and biochemical damaging events.

The harvested tissues can undergo a variety of mechanical and biochemical damaging events during procurement. Both the cellular components and the extracellular matrix can be injured during these events. Damage to the extracellular matrix occurs primarily as a result of destabilization of the cellular component. The intent of this invention is to ultimately remove this cellular component and to optimally preserve the extracellular matrix, therefore the stabilizing solution is formulated to minimize the initial cellular and subsequently the extracellular matrix damage. The extracellular protein and collagen matrix comprises a native three dimensional lattice that includes various proteins such as Type I collagen, Type II collagen, Type III collagen, Type IV collagen, elastin, laminin, teninsin and actinin, and proteoglycans.

The initiating event in cellular damage is hypoxia (deficiency of oxygen reaching tissues of the body) and a lack of nutrient supply required for the cell to maintain metabolism and energy production. Hypoxia and especially hypoxia and reperfusion results in the generation of free radicals such as hydrogen peroxide, an oxidizing species that reacts with cellular components including membranes and proteins. The subsequent changes of lipid peroxidation and crosslinking result in structural and functional derangement of the cell and initiate release of autolytic enzymes (normally contained in lysosomes) into the extracellular matrix. The damage to the matrix is two-fold, oxidant damage and enzymatic degradation. A lack of nutrient supply amplifies these events in that the cell can no longer provide the energy requirements necessary to maintain its defense mechanisms against hypoxic damage. In minimizing these events, several approaches are possible. These include the use of enzymes (superoxide dismutase and catalase) to neutralize the superoxide anion and hydrogen peroxide or compounds which can directly react with and neutralize other free-radical species. These compounds referred to as antioxidants include tertiary butylhydroquinone (BHT), alpha tocopherol, mannitol, hydroxyurea, glutathione, ascorbate, ethylenediaminetetraacetic acid (EDTA) and the amino acids histidine, proline and cysteine. In addition to antioxidants, the stabilizing solution generally contains agents to inhibit hypoxic alteration to normal biochemical pathways, for example, allopurinol to inhibit xanthine dehydrogenase, lipoxigenase inhibitors, calcium channel blocking drugs, calcium binding agents, iron binding agents, metabolic intermediaries and substrates of adenosine triphosphate (ATP) generation.

The stabilizing solution also generally contains one or more antibiotics, antifungal agents, protease inhibitors, proteoglycans, and an appropriate buffer. Antibiotics are necessary to inhibit or prevent bacterial growth and subsequent tissue infection. Antibiotics may be selected from the group of penicillin, streptomycin, gentamicin kanamycin, neomycin, bacitracin, and vancomycin. Additionally, anti-fungal agents may be employed, including amphotericin-B, nystatin and polymyxin.

Protease inhibitors are included in the stabilizing solution to inhibit endogenous proteolytic enzymes which, when released, can cause irreversible degradation of the extracellular matrix, as well as the release of chemoattractant factors. These chemoattractants solicit the involvement of polymorphonuclear leukocytes, macrophages and other killer cells which generate a nonspecific immune response that can further damage the extracellular matrix. Protease inhibitors are selected from the group consisting of N-ethylmaleimide (NEM), phenylmethylsulfonyl fluoride (PMSF), ethylenediaminetetraacetic acid (EDTA), ethylene glycol-bis (2-aminoethyl ether)-N,N,N',N'-tetraacetic acid (EGTA), leupeptin, ammonium chloride, elevated pH and apoprotinin.

Proteoglycans are included in the stabilizing solution to provide a colloid osmotic balance between the solution and the tissue, thereby preventing the diffusion of endogenous proteoglycans from the tissue to the solution. Endogenous proteoglycans serve a variety of functions in collagen-based connective tissue physiology. They may be involved in the regulation of cell growth and differentiation (e.g. heparin sulfate and smooth muscle cells) or, alternatively, they are important in preventing pathological calcification (as with heart valves). Proteoglycans are also involved in the complex regulation of collagen and elastin synthesis and remodelling, which is fundamental to connective tissue function. Proteoglycans are selected from the group of chondroitin sulfate, heparin sulfate, and dermatan sulfate. Non-proteoglycan asmotic agents which may also be included are polymers such as dextran and polyvinyl pyrolodone (PVP) and amino acids such as glycine and proline.

The stabilizing solution also generally contains an appropriate buffer. The nature of the buffer is important in several aspects of the processing technique. Crystalloid, low osmotic strength buffers have been associated with damage occurring during saphenous vein procurement and with corneal storage. Optimum pH and buffering capacity against the products of hypoxia damage (described below), is essential. In this context the organic and bicarbonate buffers have distinct advantages. (In red cell storage, acetate-citrate buffers with glycine and glucose have been shown to be effective in prolonging shelf-life and maintaining cellular integrity.) The inventors prefer to use an organic buffer selected from the group consisting of 2-(N-morpholino)ethanesulfonic acid (MES), 3-(N-morpholine)propanesulfonic acid (MPOS) and N-2-hydroxyethylpiperazine-N'-2-ethanesulfonic acid (HEPES). Alternatively, a low salt or physiological buffer, including phosphate, bicarbonate and acetate-citrate, may be more appropriate in certain applications.

In another preferred embodiment, components of the stabilizing solution address one or more of the events that occur during the harvesting of vascular tissues, such as spasm, hypoxia, hypoxia reperfusion, lysosomal enzyme release, platelet adhesion, sterility and buffering conditions. Involuntary contraction of the smooth muscle lining of a blood vessel wall can result front mechanical stretching or distension, as well as from the chemical action of certain endothelial cell derived contraction factors, typically released under hypoxic (low oxygen) conditions. This involuntary contraction results in irreversible damage to the muscle itself, the endothelial cells and the surrounding extracellular matrix. For this reason, the stabilizing solution for blood vessels includes one or more smooth muscle relaxants, selected from the group of calcitonin gene related peptide (CGRP), papaverine, sodium nitroprusside (NaNP), H7 (a protein Kinase C inhibitor) calcium channel blockers, calcium chelators, isoproterenol, phentolamine, pinacidil, isobutylmethylxanthine (IBMX), nifedepine and flurazine. The harvested tissue is immediately placed into this stabilizing solution and is maintained at 4° C. during transportation and any storage prior to further processing.

In the practice of this invention, it is essential that the harvested tissue be processed to remove antigenic cellular components.

Decellularization can be accomplished using a number of chemical treatments, including incubation in certain salts, detergents or enzymes. The use of the detergent Triton X-100, a trademarked product of Rohm and Haas Company of Philadelphia, Pa., has been demonstrated to remove cellular membranes, as detailed in U.S. Pat. No. 4,801,299. Other acceptable decellularizing detergents include polyoxyethylene (20) sorbitan mono-oleate and polyoxyethylene (80) sorbitan mono-oleate (Tween 20 and 80), sodium deoxycholate, 3-[(3-chloramidopropyl)-dimethylammino]-1-propanesulfonate, octyl-glucoside and sodium dodecyl sulfate.

Alternatively, enzymes may be used to accomplish decellularization, including but not limited to dispase II, trypsin, and thermolysin. These enzymes react with different components of collagen and intercellular connections in achieving their effects. Dispase II attacks Type IV collagen, which is a component of the lamina densa and anchoring fibrils of the basement membrane. Thermolysin attacks the bulbous phemphigoid antigen in the hemidesmosome of the basal layer of keratinocytes. Trypsin attacks the desmosome complex between cells. Due to the proteolytic nature of these enzymes, care must be taken that cellular removal occurs without significant damage to the extracellular matrix, including the basement membrane complex. This is a function of concentration, time and temperature. If used for too long a time or at too high a concentration, dispase II for example can completely remove the basement membrane complex from the dermis.

For example, with human cadaver skin Dispase II at 1.0 units/ml for 90 minutes at 37° C. will remove all keratinocytes except the basal layer, while some damage is already occurring to the basement membrane complex. Thermolysin at 200 ug/ml for 30 minutes at 4° C. will essentially remove all keratinocytes without damage to the basement membrane complex on some occasions, but this varies from donor to donor with evidence of basement membrane damage being seen in some donors. Incubation of skin in 1 molar sodium chloride for 16 hours for human skin and 48 hours for porcine skin will routinely allow clean separation of the epidermis and dermis without damage to the basement membrane complex.

In addition to salts, detergents and enzymes, the processing solution also contains certain protease inhibitors, to prevent degradation of the extracellular matrix. Collagen-based connective tissues contain proteases and collagenases as endogenous enzymes in the extracellular protein matrix. Additionally, certain cell types including smooth muscle cells, fibroblasts and endothelial cells contain a number of these enzymes inside vesicles called lysosomes. When these cells are damaged by events such as hypoxia, the lysosomes are ruptured and their contents released. As a result, the extracellular matrix can undergo severe damage from protein, proteoglycan and collagen breakdown. This damage may be severe, as evidenced in clinical cases of cardiac ischemia where a reduction in oxygen which is insufficient to cause cell death results in pronounced damage to the collagen matrix. Additionally, a consequence of extracellular breakdown is the release of chemoattractants, which solicit inflammatory cells, including polymorphonuclear leukocytes and macrophages, to the graft, which are intended to remove dead or damaged tissue. These cells also, however, perpetuate the extracellular matrix destruction through a nonspecific inflammatory response. Accordingly, the processing solution contains one or more protease inhibitors selected from the group of N-ethylmaleimide (NEM), phenylmethylsulfonylfluoride (PMSF) ethylenediamine tetraacetic acid (EDTA), ethylene glycol-bis-(2-aminoethyl(ether)NNN'N'-tetraacetic acid, ammonium chloride, elevated pH, apoprotinin and leupeptin to prevent such damage.

In addition to salts, detergents, enzymes and protease inhibitors, the processing solution generally contains an appropriate buffer. This may involve one of many different organic buffers which are described above. The inventors prefer to use an organic buffer selected from the group consisting of 2-(N-morpholino)ethanesulfonic acid (MES), Tris (hydroxymethyl)aminomethane (TRIS) and (N-[2-hydroxyethyl]piperazine-N'-[2-ethanesulfonic acid] (HEPES). Alternatively, a low salt or physiological buffer including phosphate bicarbonate acetate citrate glutamate with or without glycine, may be more appropriate in certain applications. Low salt or physiological buffers are more able to support the infiltration of the graft with viable cells and hence are more relevant when cellular infiltration including neovascularization is essential to early survival of the graft as in transplated dermal matrix.

As the processing solution may contain chemicals that would be irritating or inflammatory on transplantation, it is important to the practice of this invention that the processing solution be thoroughly rinsed from the tissue. In the preferred embodiment, this washing occurs by rinsing in sufficient changes of appropriate buffer, until residues of the processing solution are reduced to levels compatible with transplantation. Alternatively, components of the processing solution may be neutralized by specific inhibitors, e.g., dispase II by ethylenediaminetetraacetic acid (EDTA) or trypsin by serum.

The cryopreparation or freezing of the tissue takes place following thorough washing. Biological materials generally undergo significant deterioration during freezing and thawing or following freeze-drying by conventional means. Accordingly, these steps should be avoided prior to incubation of the processed, decellularized tissue in a cryoprotectant solution by the method described in this application.

The initial steps of cryopreserving the decellularized tissue includes incubating the tissue in a cryosolution prior to the freezing step. The cryosolution comprises an appropriate buffer, one or more cryoprotectants and/or dry protectants with or without an organic solvent which in combination with water undergoes neither expansion or contraction.

An appropriate buffer may involve any of the previously described buffers utilized in procurement or decellularization processing of the harvested tissue.

In addition to an appropriate buffer, the cryosolution generally contains a cryoprotectant. Cryoprotectants raise the glass transition temperature range of the tissue thereby allowing optimum stabilization of the tissue in the frozen state. By raising this range, the tissue can be dried at a faster rate. The cryoprotectant also decreases ice formation for a given cooling rate allowing to some degree vitrification (absence of a crystalline lattice), but to a greater extent, the formation of cubic ice. With current methods of ultra-rapid cooling in the absence of cryoprotectants, vitrification is only achieved with very small samples, and only to a depth of a few microns. Cubic and hexagonal ice are then encountered. Vitrified water and cubic ice are less damaging to extracellular matrix components than is hexagonal ice. In some cases, however, it is permissible to allow hexagonal ice to occur (e.g., the processing of skin). Some degree of hexagonal ice formation is permissable when it does not result in impairment of the functional characteristics of the tissue. Heart valves following implantation are subject to repetitive stress and hence will tolerate less ice crystal damage than, for example, dermis.

Various cryoprotectants can be used in the present invention. These include: dimethylsulfoxide (DMSO), dextran, sucrose, 1,2 propanediol, glycerol, sorbitol, fructose, trehalose, raffinose, propylene glycol, 2-3 butane diol, hydroxyethyl starch, polyvinylpyrrolidone (PVP), proline (or other protein stabilizers), human serum albumin and combinations thereof. Suitable cryoprotectants structure water molecules such that the freezing point is reduced and/or the rate of cooling necessary to achieve the vitreous phase is reduced. They also raise the glass transition temperature range of the vitreous state.

The cryosolution may also include exposing the biological tissue to one or more dry protectant compounds. Dry protectants, by definition, stabilize samples in the dry state. Some cryoprotectants also act as dry protectants. Some compounds possess variable amounts of each activity, e.g., trehalose is predominantly a dry protectant and a weaker cryoprotectant, whereas sucrose is predominantly a cryoprotectant and a weaker dry protectant. For example, trehalose and polyhydroxyl carbohydrates bind to and stabilize macromolecules such as proteins. Various dry protectants can be used in the present invention: sucrose, raffinose, trehalose, zinc, proline (or other protein stabilizers), myristic acid, spermine (a polyanionic compound) and combinations thereof.

The combination of 0.5 Molar dimethyl sulfoxide, 0.5M propylene glycol 0.25M 2-3 butanediol, 1.0M proline, 2.5% raffinose 15% polyvinylpyrrolidone and 15% dextran (MWT 70,000) in combination with cooling rates of the order of $-2500°$ C./second has been shown to be effective in maintaining the structural integrity of human saphenous veins following both freezing and drying. The inventors have also demonstrated that when this solution of cryoprotectants, dry protectants and buffer are used with a larger tissue sample, such as a heart valve, then the tissue can undergo cracking following freezing and/or drying. This phenomena can be overcome by replacing a percent of the water with an organic solvent such as formamide. The percent (50%) is determined as that combination of solvent, water, cryoprotectants and dry protectants which will not expand or contract during freezing. Formamide ($HCONH_2$) is a one carbon, hydrophilic, organic solvent which dissolves carbohydrate based cryoprotectants. It may be substituted with other organic solvents with similar properties such as dimethylformamide, dimethylsulfoxide (DMSO), glycerol, proplyene glycol, ethylene glycol, and pyridine.

The biological samples are incubated in the cryosolutions for a period of a few minutes to a few hours before they are rapidly cooled. In general, cryopreservation is performed as a continuous sequence of events. The tissue is first incubated in the cryosolution for a defined period (0.5 to 2 hours) until complete penetration of the components of the cryosolution is achieved and the sample is then frozen to a temperature at which it is stable, usually less than $-20°$ C.

The inventors have been involved in the development of cryofixation and ultralow temperature molecular distillation drying as a method for preparing biological samples for electron microscopic analysis. To validate this approach, they investigated the relationship between drying characteristics and ice phases present within frozen samples.

Sample preparation for electron microscopy by purely physical or dry processing techniques has theoretical appeal, especially when the ultimate aim is the analysis of both ultrastructure and biochemistry. Since the earliest days of electron microscopy, several attempts have been made to refine and develop freezing and vacuum drying or the freeze-drying (FD) process for cell and tissue samples.

Despite the conceptual advantages and the progress made, freeze-drying for electron microscopy has yet to achieve the status of a routine, broadly applicable technique. Several reasons account for this. First, the ultrastructural preservation is often inferior when compared to conventional chemical, or wet processing techniques or hybrid techniques such as freeze substitution. Second, there are numerous practical problems with sample manipulation, temperature control, vacuum parameters, and end processing protocols. Third, and perhaps most fundamentally, is a belief that drying at temperatures below $-123°$ C. to avoid ultrastructural damage is either impossible or impractical. As a result of these practical and theoretical obstacles, only sporadic investigation of low temperature freeze-drying has been reported.

The basis of this theoretical barrier comes from application of the kinetic gas theory and the predicted sublimation rates as expressed by the Knudsen equation:

$$Js = NPs \left(\frac{M}{2\pi QT}\right)^{0.5}$$

where
Js=sublimation rate
N=coefficient of evaporation
Ps=saturation vapor pressure
Q=universal gas constant
T=absolute temperature of the sample
M=molecular weight of water.

For theoretically ideal drying conditions, this equation states that the sublimation rate is directly proportional to the saturation vapor pressure of water within the sample and inversely proportional to the absolute temperature of the sample. Although the temperature of the sample is clearly definable, saturation vapor pressure is a more complex parameter.

Prior applications of this equation have used saturation vapor pressures which were theoretically determined. These theoretical vapor pressures, however, include the latent heat of fusion, and hence, are applicable only to hexagonal ice. Calculations based on these theoretical values have led to conclusions such as "at 150K it would take 3.5 years until an ice layer of 1 mm thickness is completely removed by freeze drying. It is therefore unrealistic to attempt freeze drying at temperatures below 170K."

Several phases of ice other than hexagonal, however, can coexist within a sample depending upon the mode of cooling and the use of cryoprotectants. These different phases can be achieved by several methods including; vapor condensation, hyperbaric application and ultrarapid quench cooling.

The major phases of ice now recognized are amorphous, cubic, and hexagonal. These ice phases exhibit different stabilities, which would suggest that the saturation vapor pressures would also be different. It has been determined that for vapor condensed water at temperatures where both phases can coexist, the saturation vapor pressure of amorphous ice is one to two logs higher than that of cubic ice.

Application of these experimentally determined saturation vapor pressures in the Knudsen equation reduces the drying time at 150K from 3.5 years to 0.035 years, or 12.7 days, for 1 mm of amorphous ice. Because quench cooling techniques of biological samples achieve approximately 5 μ/m din of this phase, the drying time of this component, based solely on the Knudsen equation, would be of the order of 1.5 hours. Hence, in terms of practical drying times, the theoretical barrier to drying at ultralow temperatures can be overcome.

Drying, however, is not a static, but a rate-dependent process. In addition to saturation vapor pressure of the different ice phases, one must also account for the rate of transition from one phase to another with increasing temperature. For electron microscopy sample preparation, drying should ideally occur without any such transition or devitrification. Information as to the rate of these transitions is limited. It has been found that the amorphous to cubic transition occurred as an irreversible process strongly dependent upon temperature in the range of −160° C. to −130° C. and expressed by $$t=2.04\times10^{28}\times\exp(-0.465T)$$

The cubic to hexagonal transition was less temperature-dependent, occurring in the range of −120° C. to −65° C., and expressed by $$t=2.58\times10^{12}\times\exp(-0.126T)$$

Interestingly, when the sample temperature was increased at a rate of 5° C./minute, the amorphous to cubic transition occurred as a sudden event near −130° C.

Based upon the above data, the transition rate, as well as the saturation vapor pressure, determine the depth to which a particular ice phase can be dried at a specific temperature. For amorphous ice at −160° C., the transition time is 205 days. Based upon extrapolation of experimentally determined saturation vapor pressures and the Knudsen equation, this would allow drying of 26 microns. At −140° C., transition time is 28 minutes and would allow drying of 0.8 μm under ideal conditions. Below −160° C., i.e., prior to the onset of the transition, one could predict little, if any, translational kinetic energy of the water molecules and hence little, if any, drying.

Based upon these considerations, one can postulate the hypothesis of transitional drying, i.e., that for a sample containing multiple phases of ice, it is possible to dry each phase sequentially during its transition. The amount of each phase dried will obviously be dependent upon multiple parameters including efficiency of drying apparatus, rate of heating, and impedance of the dry shell.

Cryopreservation

Cryopreservation is the preservation of cell or tissue structure against injury associated with freezing events. Natural cryoprotection can result from adaptive metabolism of the organism, with changes in cellular structure, composition and metabolic balance giving an enhanced tolerance of freezing. In laboratory experiments when cell viability or tissue ultrastructure are to be preserved following cooling, two methods are available. The first is to ultrarapidly cool the sample, resulting in the tissue fluids being vitrified, i.e., absence of ice crystals. The second is to incorporate chemical additives to confer a degree of cryoprotection. The chemicals range from naturally occurring cryoprotectants such as glycerol, proline, sugars, and alcohols to organic solvents such as dimethylsulfoxide (DMSO) to high molecular weight polymers such as polyvinylpyrrolidone (PVP), dextran and hydroxyethyl starch (HES).

Vitrification of cells and tissues is limited by the rate at which the sample can be cooled and the insulating properties of the tissue itself. Due to physical limitations, one can only achieve vitrification of a thin layer of tissues using state of the art techniques. This makes the idea of chemical additives for cryoprotection and manipulating the cooling rate very appealing in attempts to cool and store biological samples without causing structural and functional damage.

Injury to biological samples due to freezing is subject to fundamental physical and biological principles, some long known, but others only recently being understood. Serious investigations into the mechanisms of freezing injury in biological samples did not begin until the second quarter of this century. These early studies were dominated by the belief that physical damage by ice crystals was the principal cause of freeze injury. The effects of dehydration and a correlation between the concentration of extracellular solutes and cell and tissue damage has been demonstrated. A "two factor" hypothesis for cell freezing injury proposed that cell injury was the result of either the concentration of solutes by extracellular ice or the formation of intracellular ice which caused mechanical injury.

The action of glycerol and other small polar compounds has been interpreted as penetrating and exerting colligative action within the cells. In the proportion that the colligative action of the penetrating compounds maintains water in the liquid state at temperatures below 0° C., an increased volume of cellular solution is maintained. This avoids an excessive concentration of toxic electrolytes in the nonfrozen cellular solution. A similar influence also takes place in the external solution. In this context, colligative action is referred to as action by an extraneous solute, in lowering the freezing point of the solution in contact with ice. If enough protective compound is present, the salt concentration does not rise to a critically damaging level until the temperature becomes so low that the damaging reactions are slow enough to be tolerated by the cells. Similar concepts of damage to tissue matrix by both mechanical growth of ice crystals and chemical damage due to concentration of solute and changes in pH can also be applied.

The nonpenetrating cryoprotectants vary in size from sucrose to large polymeric substances such as PVP, HES and dextran. It has been suggested that nonpenetrating substances act by some other means than that in the colligative mechanism described above. The role of larger molecules is believed to be dehydrative by osmotic action. When a large proportion of water is withdrawn from the cells by means of an osmotic differential, less free water is available for intracellular ice crystallization which is often identified as a lethal factor. In tissues, polymeric substances may act by binding and structuring water molecules.

The cooling rate in the presence of cryoprotective compounds is a very important factor in freezing injury. Normally for cells, slow cooling is better than elevated cooling rates since the latter promotes intracellular ice formation. This occurs because there is insufficient time for water to escape from the cells before the contained cell water freezes. With slow rate cooling, extracellular ice forms first, resulting in dehydration of the cell which, together with the presence of the cryoprotectant, prevents intracellular ice formation. For tissue matrix samples there is a more direct correlation to the overall reduction in the degree of total ice crystal formation.

Penetrating compounds were thought to act by not allowing an excessive transport of water from the cells too early in the freezing process while nonpenetrating compounds have a dehydrative effect on cells along with a colligative effect of diluting the solution surrounding the cell. Neither of these descriptions, however, tells the whole story.

Solutes such as HES and PVP are totally nonpenetrating, water withdrawing compounds of merely larger molecular weight than nonpenetrating sucrose. The larger molecular weight should render such compounds less osmotically and colligatively effective, when considered on a weight basis. Yet in concentrated solutions, the compounds' colligative action has been shown to be far greater than would be expected based on merely a linear relationship to concentration.

A source of damage to frozen tissue, other than freezing itself, is the osmotic and toxic effects of many of the cryoprotective agents. When used in mixtures, some cryoprotective compounds may counteract the toxicity of other cryoprotectants, as was demonstrated by the addition of polyethylene glycol (PEG) to a mixture of DMSO and glycerol. The inventors have developed several vitrification solutions (VS).

The toxicity of the individual components of these solutions were tested. In the mixtures, the toxic effects were lower than when an equivalent concentration of any one component was used alone. The resulting solutions are nontoxic to cell cultures and remains glass like and optically clear (i.e., no visible ice crystal is formed) when plunged into liquid nitrogen.

| Vitrification Solution 1 | |
| --- | --- |
| Dimethylsulfoxide (DMSO) | 0.5M |
| Propylene glycol | 0.5M |
| 2-3 butanediol | 0.25M |
| Proline | 1.0M |
| Raffinose | 2.5% (w/v) |
| Polyvinylpyrrolidone (PVP) | 15% (w/v) (Ave. M.W. $\approx$ 40,000) |
| Dextran | 15% (w/v) (Ave. M.W. $\approx$ 40,000-70,000) |

A modified vitrification solution ($VS_2$) has also been developed which comprises a mixture of:

| | |
| --- | --- |
| DMSO | 0.5M |
| Propylene glycol | 0.5M |
| 2-3 butanediol | 0.25M |
| Raffinose | 10% (w/v) |
| Trehalose | 6% (w/v) |
| Sucrose | 6% (w/v) |
| PVP | 12% (w/v) (Ave. M.W. $\approx$ 40,000) |
| Dextran | 12% (w/v) (Ave. M.W. $\approx$ 40,000-70,000) |

Another modified vitrification solution ($VS_3$) which has been developed comprises a mixture of:

| | |
| --- | --- |
| DMSO | 0.5M |
| Propylene glycol | 0.5M |
| 2-3 butanediol | 0.25M |
| Raffinose | 25% (w/v) |
| Sucrose | 12% (w/v) |
| PVP | 15% (w/v) (Ave. M.W. $\approx$ 40,000) |
| Dextran | 15% (w/v) (Ave. M.W. $\approx$ 40,000-70,000) |

A fourth modified solution ($VS_4$) has been developed. This solution differs in that it contains 50% formamide, an organic solvent. This mixture neither expands nor contracts with freezing and hence does not cause cracking when freezing larger tissue samples. It comprises a mixture of:

| | |
| --- | --- |
| Formamide | 50% (w/v) |
| 70K Dextran | 15% (w/v) |
| Raffinose | 2.5% (w/v) |
| 40K PVP | 15% (w/v) |
| Sucrose | 12% (w/v) |

In summary, the factors affecting the cryoprotective nature of compounds are (a) chemical composition, (b) low toxicity, (c) molecular size and penetrating ability, and (d) interaction with other compounds in the mixture.

The physicochemical effects of cryoprotectants are (a) depression of the equilibrium freezing point of substrate and cytoplasm on a colligative basis, (b) depression of homogeneous ice nucleation temperature, (c) reduced rate of ice crystal growth due to change in the viscosity and thermal diffusivity of the solution, and (d) dehydrative effects on cells by osmotic action.

Cooling Parameters

For purposes of cryopreparation of the biological tissues of this invention, it is essential to note that a variety of cooling processes can be used. In a preferred embodiment of this invention, rapid cooling is considered essential to obtain the proper ice crystal blend. In the most preferred embodiment of this invention, a vitrification procedure is used which results in the formation of a substantial proportion of amorphous water in the biological sample. As will be disclosed hereinafter, regardless of the form of cooling that is used, it is believed that amorphous phase water, cubic ice crystals and hexagonal ice crystals are present in the final product. The method of cooling has a distinct bearing on the distribution of ice crystal types found in the cooled cryosolution.

Drying Parameters

The aim of controlled drying of a frozen biological tissue by molecular distillation drying is to remove water from the sample without further mechanical or chemical damage occurring during the drying process. This involves avoiding, by use of appropriate drying conditions, two fundamental damaging events. The first is to remove water from ice crystalline phases without transition to larger more stable and more destructive crystals. The second is to remove water from solid but noncrystalline water or water-solute mixtures without melting or crystallization of these solid phases. This second component refers to water present in the amorphous condition, water together with solute in the eutectic or water together with a compound which binds and structures water and hence, prevents its crystallization during the freezing process. Hence, vitreous water can be of low energy and stability, as in ultrarapidly-cooled pure water, or high energy and stability, as that achieved with cryoprotective agents with intermediate rates of cooling.

Many of the features required of controlled drying to avoid the occurrence of these events are overlapping. The reason for this is that each form of water will have a particular energy state, whether in a crystal or bound to a cryoprotective compound, and it is this energy state, rather than its configuration, which determines the requirements for drying. Consider for example, (1) a sample of cubic ice achieved by cooling pure water at an intermediate cooling rate and (2) vitrified water achieved by mixing water with glycerol to 45% vol:vol and cooling at an intermediate rate. The first sample will be crystalline and the aim of drying is to remove water from this state without transition to hexagonal ice. The second sample is an amorphous solid and the aim of drying is to remove water from this phase without melting of the glass to a liquid with subsequent boiling. For cubic ice, the onset of its transition is $-130°$ C. and the rate of transition is temperature dependent being very slow at $-130°$ C. and very rapid at $-90°$ C. For 45% glycerol-water, the glass transition temperature is $-120°$ C. and represents the onset of melting. The melting process is very slow at $-120°$ C. and is temperature dependent, becoming very rapid at $-90°$ C.

Prior to the onset of the cubic to hexagonal transition or the glass transition of 45% glycerol-water, the saturation vapor pressure of water in these phases is extremely low and drying would occur at extremely slow rates. The aim of controlled drying, therefore, is to remove water from the cubic ice phase during its transition and in a time less than is required for any significant transition to hexagonal ice and from the 45% glycerol-water phase during its transition to a liquid but in less time than is required for any appreciable liquid to form.

This argument can be applied repetitively to all forms of water present whether it be crystalline in the form of cubic or hexagonal or noncrystalline as amorphous or bound to any molecule, be it cryoprotectant, protein, carbohydrate, or lipid. To simplify this concept, water in a frozen biological sample can be described as having a specific energy level E. In a frozen biological sample, there will be water forms of multiple definable energy levels:

$$E_1 E_2 E_3 \text{ - - - } E_n$$

The mode of preparation, the nature of the sample, the use of cryoprotectants or other additives, and the cooling rate used will determine the relative proportions of these different water forms. Each energy level will determine the onset temperature of its transition or melting and the temperature dependence of the rate of the transition or melt.

Controlled drying processes must be able to remove each of these different states of water during the transition and in less time than is required to complete the transition. This mode of drying, therefore, requires that several conditions be met.

First, the frozen sample must be loaded into the dryer without temperature elevation above its lowest transition temperature. If elevation of temperature does occur, this must be over a short period of time such that no appreciable transition occurs. Ideally, loading occurs under liquid nitrogen at $-190°$ C., well below the lowest discernible transition of $-160°$ C. for pure, ultrarapidly-cooled amorphous water. If, however, the sample is predominantly cubic ice or a mixture of water and cryoprotectants with a glass transition of the order of $-100°$ C. to $-130°$ C., a closed circuit refrigeration system may be sufficient to enable maintenance of the sample temperature below the onset of transition.

Once loaded, the sample must be exposed to vacuum and be in direct line of sight of the condenser surfaces. The criteria for these are again determined by the nature of the water phases present in the sample. The following objectives must be attained. The vacuum within the chamber during the drying of a particular phase must create a partial pressure of water at least equivalent to or less than the saturation vapor pressure of water in the phase to be removed. This saturation vapor pressure is dependent on the nature of the water phase and its temperature. Hence, for pure amorphous water in the transition range of $-160°$ C. to $-130°$ C., the approximate saturation vapor pressures are $6 \times 10^{-12}$ mbar ($-160°$ C.) and $5 \times 10^{-7}$ mbar ($-130°$ C.), respectively. As the transition times of amorphous to cubic ice in this same temperature range, $-160°$ C. to $-130°$ C., vary from $5 \times 10^5$ minutes to 5 minutes, drying will be very slow until temperatures of the order of $-150°$ C. to $-140°$ C. are reached requiring a vacuum of $5\times10^{-10}$ to $2\times10^{-8}$ mbar. This represents one extreme.

For cubic ice, little if any drying will occur below its onset of transition at $-130°$ C. as its saturation vapor pressure will be of the order of one log lower than for amorphous water. In the transition range, $-130°$ C. to $-100°$ C., the saturation vapor pressure of cubic ice is approximately $5\times10^{-8}$ to $9\times10^{-5}$ mbar. The transition times of cubic to hexagonal are 700 minutes and 109 minutes respectively. The saturation vapor pressure, therefore, determines the vacuum requirements for drying and can be applied to all water phases present. It is important to note that the same vacuum criteria are not applicable to all phases, but rather are phase-dependent.

A second criteria of the vacuum is that the mean free path be in excess of the distance between the sample and the condenser surface. Ideally, this should be a tenfold excess. The condenser surface must be a lower temperature than the onset transition temperature of the phase of water being removed from the sample so that the saturation vapor pressure of water condensed on this surface during drying is considerably lower than that of the water phase within the sample. Ideally, this should be three orders of magnitude lower. For a sample containing multiple water phases, the temperature of the condenser surface must remain below the onset of transition of the least stable ice phase remaining to be removed. Ideally, the condenser should also be in line of sight of the sample.

Once the sample has been loaded and exposed to vacuum and the condenser surfaces, the sample and sample holder must be heated so as to increase the mobility of water molecules and hence, cause their escape. This is the essential and critical component in the drying of a sample containing multiple phases or energy levels of water. The temperature of the sample must be accurately known. The control of temperature and the rate of sample heating must be accurately controlled. This is necessary to ensure that the drying of each phase of water in the sample is sequential.

Hence, for a sample containing multiple phases of water of energy level $E_1$, and $E_2 - - - E_n$ where $E_1$ is the least stable, then heating must occur at such a rate that $E_1$ is removed prior to its transition to $E_2$. $E_2$ prior to its transition to $E_3$ and so on. This requires nonequilibrium drying conditions and heating at a continuous rate or by holding at a constant temperature level such that sublimation occurs as determined by:

$$Js = NPs \left(\frac{M}{2\pi QT}\right)^{0.5}$$

where
- $Js$ = sublimation rate in g cm$^{-1}$ sec$^{-1}$
- $N$ = coefficient of evaporation
- $Ps$ = saturation vapor pressure
- $M$ = molecular weight of water
- $Q$ = universal gas constant
- $T$ = absolute temperature of the sample.

This is consistent with the transition rate for the particular phase being removed. For example, the rate of the amorphous to cubic transition is given by:

$$E = 2.04\times10^{28}\times\exp(-0.465T)$$

Alternatively, if the transition window is $T_1$ to $T_2$, the sublimation rate and the transition rate will vary with temperature during this interval. The rate of heating during this window $T_1$ to $T_2$ must be such that sublimation occurs throughout the dimensions of the sample before transition at any particular temperature is completed.

In this way, the aim of controlled drying is achieved, i.e., the sequential removal of each phase of water under conditions appropriate to the properties of each phase without appreciable ice crystal growth, formation or melting of the particular phase. Once dry, the sample must be physically or mechanically isolated from water on the condenser surface or any other source and stored in a closed container either under vacuum or dry inert gas.

In a preferred embodiment, samples are cooled by an appropriate method such that ice crystal formation is below the degree that would cause damage to the sample. Once frozen, the sample is then stored below the transition temperature of the most unstable ice form. For amorphous ice, this is preferentially below $-160°$ C. The sample is then loaded into a sample holder, precooled to $-196°$ C. and transferred into a molecular distillation dryer. The dryer chamber is then closed and sealed for vacuum integrity. To avoid recrystallization, the hydrated sample must remain below the transition temperature of the most unstable ice form throughout all manipulations.

Once the sample is loaded, high vacuum ($10^{-8}$ to $10^{-6}$ mbar) is generated inside the chamber. The sample is placed considerably closer to the condenser surface (liquid nitrogen cooled chamber walls) than the mean free path within the chamber. The condenser temperature must always be below that of the sample. For an amorphous sample, the condenser is preferentially $-196°$ C.

The sample holder is then heated via a programmable heater microprocessor thermocouple loop. Heating programs are determined according to the ice composition of the sample. A typical program for a sample containing amorphous, cubic and hexagonal ice is 10° C. per hour from $-180°$ C. to $-150°$ C., per hour from $-150°$ C. to $-70°$ C., and 10° C. per hour from $-70°$ C. to $+20°$ C.

Once the sample has reached 20° C, it can be sealed inside an appropriate container within the vacuum chamber and unloaded for subsequent storage. In one configuration, the sample is contained within a glass vial and sealed with a butylrubber lyophilization stopper at the end of cycle. More specific details of the operation of the molecular distillation dryer are given in U.S. Pat. No. 4,865,871.

Reconstitution

The freezing and drying of biological tissues impart great physical stress upon the bonding forces which normally stabilize macromolecular conformation. Contributing to this destabilizing effect is the increase in concentration of electrolytes and possible pH changes as the solution freezes. As a consequence, modifications to the sample, including the inactivation of certain enzymes, and the denaturation of proteins, may result.

Studies with lactic dehydrogenase have shown that freezing and thawing cause dissociation of the tetrameric enzyme into subunits which is accompanied by a change in biological activity. The dissociation was found to be dependent on the ionic strength and pH during freezing.

Other studies investigating the quaternary structure of L-asparaginase demonstrated that this enzyme dissociated from the active tetramer to inactive monomers when freeze-dried. This monomeric state was found to be stabilized by reconstitution of the dried enzyme with buffers of high pH and high ionic strength. However, the dissociation was shown to be completely reversible on reconstitution at neutral pH and low ionic strength. The effect of pH on the other hand may induce changes in the three dimensional structure resulting in subunits conformationally restrained from reassociation.

These studies indicate the importance of determining optimal pH and ionic strength conditions of not only the formulation used in the cryopreservation protocol, but also the reconstitution solution. In this way, maximal sample activity and stability may be obtained.

Other variables of reconstitution such as vapor phase rehydration or temperature may also be important to the retention of activity following freezing and drying. Other workers in the field have demonstrated a marked difference in proliferative response to lectins depending on the temperature of rehydration or whether samples were reconstituted by vapor phase. Improved responses to lectins were noted when the freeze-dried lymphocytes were rehydrated at dry ice temperatures and then allowed to warm. This gradual method of reconstitution reduced the osmotic stress induced by sudden rehydration.

In the processing of biological tissues, the rehydration step can also be used to augment the processing and stabilization compounds used in the procurement and processing steps. These include components to minimize the effects of hypoxia and free radical generation, agents to inhibit enzymes, oncotic agents including proteoglycans, dextran and amino acids to prevent osmotic damage.

In addition, the rehydration of certain tissues, e.g., the vascular conduits and heart valves, may require specific agents to inhibit plaletet aggregation during the early post implant period. Where the biological tissue is to be crosslinked, rehydration directly in the fixative has the additional advantage of immediate and uniform distribution of the fixative throughout the tissue.

Storage Considerations

Sublimation of water from a frozen sample is one method for preserving the active components of biological material. However, the optimal preservation of activity with long-term stability requires critical control of the drying process and storage conditions. Following the removal of free or unbound water, the process of secondary drying proceeds, during which structurally bound water is removed. Bound water is intimately associated with the maintenance of protein conformation. Thus, the amount of water remaining in the dried sample, known as the residual moisture content, is a significant variable in the drying process. The final residual moisture content affects both the survival and stability of the sample.

Residual moisture content is expressed as the "percentage residual moisture" and is equated to the weight (gin) of residual water per unit weight (gin) of original sample.

It is generally agreed that biological materials dried by vacuum sublimation of ice show increased stabilization when dried to optimum contents of residual moisture. Materials which have been under or overdried, i.e., to moisture contents that are above or below the optimum, will show increased deterioration.

Although the optimal residual moisture content will vary depending on the particular dried sample, certain stability problems can be expected when the levels of moisture are suboptimal. Overdrying a sample, i.e., residual moisture contents less than 1-2% without using a dry stabilizer, generally results in removal of nearly all structured water allowing modification or blocking of exposed hydrophilic sites of proteins by oxidation. This oxidation causes degradation with a corresponding decrease in the biological activity. On the other hand, residual moisture contents of greater than 5% generally are indicative of underdrying where sufficient amounts of "free water" remain in the sample which could contribute to transconformation of the protein. The resulting rearrangements of the polypeptide chains shift from the typical ordered arrangement of the native protein to a more disordered arrangement. These protein perturbations can result in poor long-term stability of the dried product.

Successful long-term storage requires sample drying to optimal levels of residual moisture. Inadequate drying of biological samples and its consequences have been shown in the literature. Maximal stability of suspensions of influenza virus dried by sublimation of water in vacuo occurred at a residual moisture content of approximately 1.7%. Under or over drying to non-optimal water content resulted in the degradation of the virus suggesting that varying amounts of free and bound water in a dried sample have an effect upon protein structure and activity.

To maximize sample stability and satisfy regulatory requirements for the preparation of dried pharmaceuticals or reagents, it is essential that the residual moisture content be determined following sample drying.

Several methods are available to measure residual moisture contents;

1. Gravimetric (Heating Method)—A known quantity of dried product is heated and the weight loss can be equated with water content.
2. Chemical Assay—This method is based on the reaction between water and free iodine in a mixture of pyridine, sulphur dioxide and methanol. The endpoint is detected coulometrically when free iodine is present. $H_2O+I_2+SO_2+ROH+3RN \rightarrow 2RNHI+RN+HSO_4R$
3. Gas Chromatography Each of the methods has limitations and therefore, it is wise to not rely on any single method of moisture determination. Rather, multiple methods should be employed to validate the results.

Once dried to optimal residual moisture contents, the sample is still considered unstable when removed from the vacuum due to its hygroscopic nature and susceptibility to oxidation. Measures must be taken during storage to protect the sample from atmospheric rehydration and minimize exposure to oxygen. Such protection is essential to the maintenance of the sample's long-term stability.

Evidence in the literature indicates that the gaseous condition under which the samples are sealed, as well as the storage temperature, effects the long-term stability of the sample. It has been demonstrated in a study comparing different gases and storage temperatures, that maximum stability of influenza virus was obtained when samples were stored under helium or hydrogen gas at low temperature (−20° C.). Sealing under other gases or vacuum at different storage temperatures resulted in varying levels of stability. The inventors postulate that those conditions which most effectively limit oxygen contact with the sample, markedly improve biological activity by reducing oxidation of exposed hydrophilic sites at the protein surface. Appropriate storage parameters, i.e., temperature, and sealing under gas or vacuum are important to obtain long-term sample stability.

EXAMPLE 1

PROCESSING AND STORAGE OF TRANSPLANTABLE SKIN

Human donor skin is routinely harvested from cadavers and stored under refrigerated or frozen conditions at a number of tissue banks throughout the nation. This skin is used as a temporary dressing for burn victims that are undergoing extensive autografting. Porcine skin is also harvested under similar conditions and used as a temporary burn dressing. In its unprocessed condition, the allogeneic skin and porcine skin are ultimately rejected by the patient. This same skin is also available for processing by the methods described below.

Donor skin is harvested under aseptic conditions with a dermatome, and maintained at 4° C. in RPMI 1640 tissue culture media containing penicillin and streptomycin solution for no more than 7 days prior to further processing. Transportation to LifeCell's tissue processing center is via overnight delivery, on wet ice, in the same media. On arrival at the processing center, the temperature of the tissue container is verified to be at least 4°, or the skin discarded. Following verification of container temperature, donor identification and test screening data, the skin is transferred to a laminar-flow hood for further processing.

The donor skin is removed from the transportation container and placed with its reticular side down on a piece of sizing support being a low density polyethylene. An appropriately sized piece of gauze is added to the epidermal side of the skin which is then cut into a rectangular piece as large as possible, not to exceed a 4×4 inch square and no smaller than 2×3 inches. The skin is then placed reticular side down, in a petri dish, to which 50 ml of De-epidermizing Solution consisting of 1M NaCl is added. The petri dish is then transferred to an incubator and incubated at 37°±2° C. for 18 to 32 hours for human skin and 35 to 55 hours for porcine skin.

After incubation, the petri dish containing the skin is transferred to a laminar flow hood for deepidermization. The gauze is first removed and discarded. The epidermis is then gently grasped with forceps and pulled away from dermis as a sheet. The excess Deepiderizing Solution is then aspirated. A slit approximately one centimeter long is then made in the lower left corner of the dermis to identify the upper and lower surfaces.

The dermis is next rinsed in the same petri dish by the addition of 50 ml Tissue Wash Solution, consisting of sterile Hanks balanced salt solution. The petri dish is then placed on a rotator at 40±5 RPM for 5 minutes at room temperature (20°–26° C.). The petri dish is then returned to the laminar flow hood and the lid from the petri dish is removed in order to aspirate the Tissue Wash Solution. This procedure is repeated a further two times.

The dermis is then treated with 50 ml. of De-Cellularizing solution and the petri dish is placed on a rotator at 40±5 RPM for 1 hour at room temperature (20°–26° C.). The decellarizing solution for human skin consists of 0.5% sodium dodecyl sulfate in Hanks balanced salt solution and for porcine skin contains 1 mM disodium ethylenediamine tetraacetic acid (EDTA). The De-cellularizing solution is removed by aspiration. The dermis is then washed with 50ml of Tissue Wash Solution. The petri dish is then placed on a rotator at 40±5 RPM for 5 minutes at room temperature (20°–26° C.). The Tissue Wash Solution is removed by aspiration. The washing procedure is repeated (2) times. After the dermis has been washed a total of 3 times 50 ml of Prefreezing Solution is added to the petri dish. The dish is then placed on a rotator at 40±5 RPM for 30 minutes at room temperature (20°–26° C.). The prefreezing solution for human skin consists of 7% dextran (70,000 MWT), 6% sucrose, 6% raffinose and 1 mM disodium ethylenediamine tetraacetic acid in Hanks balanced salt solution. The prefreezing solution for porcine skin consists of 7.5% dextran (70,000 MWT), 6% sucrose, 7.5% polyvinylpyrrolidone (MWT 40,000), 1.25% raffinose and 1 mM disodium ethylenediamine tetraacetic acid made up in Hanks balanced salt solution.

A new piece of gauze is then placed on the papillary side of the dermis and the dermis is turned over so that the reticular side faces up. The backing from the reticular side of the piece of dermis is discarded into a biohazard waste container. An approximately 0.5 to 1.0 cm wide strip of backing and dermis is then cut from the original sample. This strip is then cut into two satellite pieces, each approximately 1.0 cm long. All necessary quality assurance is ultimately performed on these satellite samples, including microbiology and structural analysis.

The tissues are then transferred into individual Tyvec bags. The tissues are positioned in the bag backing side up with the white vent side down. The Tyvec bag is then heat sealed.

The sealed Freeze-dry Bag is transferred to a freeze-dryer which has a minimum shelf temperature of −70° C. and a minimum condenser temperature of −85° C. The tissue is then frozen on the freeze-dryer shelf by ramping the shelf temperature at a rate of −2.5° C./minute to −35° C., and held for at least 10 minutes.

The drying cycle is such that the final residual moisture content of the sample is less than 6% and optimally 2%. In this example, the frozen dermis is dried by the following program:

1. The shelf temperature is ramped at a rate of −2.5° C./minute to −35° C., and held for 10 minutes, with vacuum set to 2000 mT.
2. The shelf temperature is then ramped at a rate of 1.5° C./minute to −23° C., and held for 36 hours with vacuum set to 2000mT.
3. The temperature is then ramped at rate of 1.5° C./minute to a shelf temperature of −15° C., and held for 180 minutes with vacuum set to 2000 mT.
4. The temperature is then ramped at a rate of 1.5° C./minute to a shelf temperature of −5° C. and held for 180 minutes with vacuum set to 2000 mT.
5. The temperature is finally ramped at a rate of 1.5° C./minute to a shelf temperature of 20° C. and held for 180 minutes with the vacuum set to 0 mT.

Following drying, the Freeze-dry Bag containing the dried dermis is unloaded under an atmosphere of dry nitrogen gas, placed in a second predried impervious pouch and heat sealed under the same inert environment.

(During the processing procedure and prior to sealing for freeze drying, a satellite sample is cut from the main sample and further processed under identical conditions to the main sample. Prior to use of the main sample in transplantation, all necessary quality assurance is performed on the satellite sample, including microbiology and structural analysis.)

Following drying, the sample is stored at above freezing temperatures, optimally 4° C. in a light protected environment.

Prior to use, the sample is removed from the sealed pouch under aseptic conditions and rehydrated by immersion in balanced salt solution at 20° to 37° C. Rehydration is complete after 30 minutes of incubation in this rehydration solution.

Analysis of the end product by light and electron microscopy has demonstrated it to be structurally intact with normal collagen banding and the presence of collagen bundles in the matrix of the dermis and with structural preservation of the lamina densa and anchoring fibrils of basement membrane complex.

The reticular aspect of processed dermis has been demonstrated to provide a substratum for the outgrowth of keratinocytes from a foreskin explant in a laboratory by cell culture methods. The processed dermis has also been demonstrated to support the growth of isolated keratinocytes. In this circumstance, when cultured at an air liquid interface, keratinocytes differentiate to all identifiable layers of normal skin and interact with the processed dermis through the basement membrane complex. Processed porcine skin has also been demonstrated to support the growth of keratinocytes from human foreskin explants.

The processed dermis, either in combination with a meshed, ultra thin or epidermal autologous graft or reconstituted with cultured keratinocytes, has a number of clinical applications in full thickness skin injury. These include, but are not limited to, burn patients, patients suffering from venous, diabetic, or pressure ulcers, and patients who undergo reconstructive surgery, or skin replacement following excision of skin lesions.

Processed human and porcine skin have been shown to undergo fibroblast infiltration and neovascularization in human burns patients and in surgically induced full thickness skin injury in pigs.

EXAMPLE 2

VASCULAR CONDUIT: HUMAN DONOR SAPHENOUS VEINS

Saphenous veins are harvested from cadaver donors and made available by tissue banks across the U.S. Tissue banks have established procurement guidelines, published by the American Association of Tissue Banks. These guidelines include instructions for patient selection, completion of consent forms and a caution to avoid mechanical distention or other mechanical damage to the vein during the dissection process.

Harvesting begins with flushing and distension of the vein with Vein Flushing Solution, consisting of 1000 cc PlasmaLyte Solution for injection, amended with 5000 units of Heparin and 120 mg of Papaverine (1 liter per vein). The veins are carefully removed under sterile conditions with as many tributaries maintained intact as possible, with a length of at least 5 min. These tributaries are ligated with 3-0 silk. The surrounding fatty tissue is also maintained with wide margins around the vein. Once the vein is removed, it is rinsed again with Vein Flushing Solution, packaged in 500 cc of cold (4° C.) Vein Transport Medium, consisting of 500 cc RPMI 1640 Tissue Culture Medium amended with 60 mg Papaverine and shipped by overnight delivery to a tissue bank for further processing.

At the tissue bank, all tributaries are suture ligated and the subcutaneous fat/soft tissue removed using standard surgical procedures. Following dissection, the vein is disinfected of any surface contaminants by placing it in a tissue culture medium amended with Cefoxitin (240 mcg/ml), Lincomycin (120 mcg/ml), Polymyxin B Sulfate (100 mcg/ml) and Vancomycin (50 mcg/ml). The vein is maintained in the antibiotic mixture at 4° C. for 24 hours. The disinfected vein is placed in 500 cc of cold (4° C.) Transport Medium, consisting of 500 cc RPMI 1640 Tissue Culture Medium and transported on wet ice to LifeCell's Tissue Processing Center by overnight delivery.

On arrival, the container temperature is verified to be at least 4° C. Following verification, the vein is placed into a container containing Cryosolution and incubated for one hour at room temperature. The Cryosolution consists of the following:

0.5M Dimethyl Sulfoxide (DMSO)
0.5M Propylene Glycol
0.25M 2-3 Butanediol
2.5% (w/v) Raffinose
12.0% (w/v) Sucrose
15.0% (w/v) Polyvinylpyrrolidone (PVP)
15.0% Dextran.

After incubation, the vein is then placed into an inert plastic bag containing a porous vent which allows water vapor to pass out, but prevents bacteria from passing in and is heat sealed. The bag and vein is then frozen by plunging into liquid nitrogen. The frozen vein is stored at temperatures below $-160°$ C.

For drying, the frozen vein within the bag is transferred under liquid nitrogen to a molecular distillation dryer, and dried by methods described in U.S. Pat. No. 4,865,871. For saphenous veins processed in the above described cryosolution and rapidly frozen, the optimum range for drying is $-130°$ C. to $-70°$ C. with a heating rate of 1° C. per minute during the drying phase. Once dry, the vein is sealed in the container under dry inert nitrogen gas and stored at refrigerated temperatures (2°-4° C.) until needed for transplantation.

The vein is rehydrated in a vapor phase, by opening the plastic pouch container and placing the vein in a 37° C. humidified incubator. The vein is maintained in this incubator for one hour, after which it is removed and placed in a container with phosphate buffered saline (PBS). The vein is then rinsed with 3 changes of PBS.

Analysis of the processed veins show them to possess an intact extracellular matrix both by light and electron microscopy. Protease digestion indicates no increased susceptibility of collagen to degradation. Stress testing on a dynamic loop with an artificial heart has demonstrated them to withstand supraphysiological pressures without compromise of their leak barrier function to either liquid or gas.

EXAMPLE 3

VASCULAR CONDUIT PROCESSING FOR ANIMAL STUDY

Procurement

Twenty to thirty kilogram mongrel dogs of either sex are induced via sodium pentathol, intubated, and prepped and draped in a sterile fashion. Anaesthesia is maintained with oxygen, nitrogen, and Halothane. A midline incision is made in the neck whereupon the external jugular veins and internal carotid arteries are exposed, isolated, and freed of surrounding fascia. During this procedure, a flushing solution comprised of 5000 units of heparin and 120 mg of Papavarine in 1000 cc sterile Hank's Buffered Saline Solution (HBSS) of pH 7.4 is sprayed on the vessels via a needle and syringe. The proximal and distal ends of the vessel are then clamped with atraumatic vascular clamps whereupon the vessel is rapidly excised. Immediately the vessel is flushed through and through with the above mentioned flushing solution and placed in 4° C. flushing solution for transport. Alternatively, the vessel may be placed in the below mentioned Decellularization Solution A for incubation during transport.

Decellularization

After the trimming of any excess fascia, the vessel is placed in Decellularization Solution A (DSA). DSA is comprised of 25 mM EDTA, 1 M NaCl, and 8 mM CHAPS or similar zwitterionic detergent in a sterile PBS base at 7.5 pH. After a 30 minute to one hour incubation, the vessel is given two ten minute washes in PBS and then placed in Decellularization Solution B (DSB). DSB is comprised of 25 mM EDTA, 1M NaCl, and 1.8 mM Sodium Dodecylsulfate (SDS) or similar anionic or nonionic detergent in a sterile PBS base at 7.5 pH. After a 30 minute to one hour incubation, the vessel is given two ten minute washes in PBS.

Vitrification

After decellularization, the vessel is placed in Vitrification Solution Fifty-fifty (VSFF) for one to five hours. VSFF is comprised of 2.5% raffinose, 15% polyvinylpyrrolidone (PVP) of 40,000 molecular weight, 15% Dextran of 70,000 molecular weight, and 12% sucrose in a 50/50 (by volume) water-formamide solution. The vessel is then rapidly submerged in liquid nitrogen ($LN_2$) until frozen as evidenced by the cessation of boiling. The vessel may then be stored in $LN_2$ or $LN_2$ vapor, or immediately dried.

Drying

After vitrification, the vessel is transferred in a nitrogen gas atmosphere to a special Molecular Distillation Dryer sample holder which has been pre-cooled to −196° C. The sample holder is then rapidly transferred under nitrogen gas atmosphere to the Molecular Distillation Dryer. The dryer is then evacuated and run according to a protocol developed specifically for VSFF. Under a vacuum less than $1 \times 10^{-6}$ mbar, the sample holder is warmed according to the following protocol:
- −196° C.→−150° C. over 10 hours
- −150° C.→−70° C. over 80 hours
- −70° C.→20° C. over 10 hours The dryer is then opened and the vessel is transferred to a sealed sterile glass vial under nitrogen gas atmosphere. The vessel is then stored at 4° C. until needed.

Rehydration

Twenty-four hours prior to use, the glass vial is opened in a 100% humidity, 37° C. atmosphere. The vessel is allowed to vapor rehydrate in this manner for one to two hours. The vessel is then submerged in sterile PBS at 4° C. for two hours. The PBS is then exchanged with fresh solution whereupon the vessel is stored at 4° C. overnight. The vessel is ready for use the following day.

EXAMPLE 4

PORCINE HEART VALE LEAFLETS

Porcine heart valves were obtained from isolated hearts immediately following slaughter at an abattoir. Discs from the leaflets of the intact valve were obtained by punch biopsy under aseptic conditions and transferred to a transportation solution comprising Dulbecco's PBS with 5.6 mM glucose, 0.33 mM sodium pyruvate with added anti-oxidants comprising 0.025 mg/l alpha-tocophenol phosphate, 50 mg/l ascorbic acid and 10 mg/l glutathione (monosodium) at 4° C.

Upon receipt of tissue, the discs were transferred to a cryosolution comprising 0.5M DMSO, 0.5M propylene glycol, 0.25M 2-3 butanediol, 2-5% raffinose, 15% polyvinyl pyrrolodone, 15% Dextran and 12% sucrose and incubated at 20° C. for 60 minutes with moderate agitation.

Tissue samples were then placed on thin copper substrates matching the size of the tissue sample and cooled by immersion in liquid nitrogen.

The frozen samples were then stored at below −160° C. until further processing.

Prior to drying, the samples were transferred under liquid nitrogen to a sample holder equipped with thermocouple and heater. The sample holder was precooled to liquid nitrogen temperature, and the transfer was completed under liquid nitrogen.

The frozen samples were then loaded into a molecular distillation dryer and dried by molecular distillation drying employing the method described in U.S. Pat. No. 4,865,871. The drying cycle employed was −180° C. to −150° C. in 3 hours, −150° C. to −70° C. in 80 hours and −70° C. to +20° C. in 9 hours. Following drying, the vacuum in the drying chamber was reversed with ultrapure nitrogen gas and the discs maintained in this atmosphere until processing. Rehydration of the dry samples first consisted of exposure of samples to 100% humidity at 37° C. for 60 minutes. Samples were then rehydrated in a rehydration solution which consisted of one of the following:

a. 0.06M Hepes buffer
b. 0.06M Hepes buffer + 0.06M $MgCl_2$
c. 0.06M Hepes buffer + 1% SDS
d. 0.06M Hepes buffer + 0.5 mM PMSF Samples were incubated with agitation for at least four hours.

Following rehydration, samples were assessed under the following criteria:
a. Structure was assessed by both light and electron microscopy and the valve matrix was found to be indistinguishable from that of fresh unprocessed samples.
b. Protease digestion was found to be equivalent to fresh sample.
c. Stress testing (static) was found to be able to withstand greater stress load than control samples.
d. Subcutaneous animal implant model with subsequent explant at 7 or 21 days.

Explanted samples demonstrated:
 i. Decreased capsule formation relative to fresh or cryopreserved controls
 ii. Decreased calcification relative to glutaraldehyde treated controls
 iii. Variable inflammatory cell infiltration depending on the nature of the rehydration solution as follows:

Treatment: 0.06M $MgCl_2$ in 0.06M Hepes buffer

Clearly demarcated disc with well defined normal valve morphology. Sample incompletely surrounded by thin capsule with minimal inflammatory cell infiltration near disc periphery.

Treatment: 1% SDS in 0.06M Hepes buffer

Clearly demarcated disc with well defined normal valve morphology. Sample completely surrounded by a slightly thicker capsule than that observed in MgCl$_2$ treated sample. Minimal inflammatory cell infiltration.
Treatment: 0.5 mM PMSF in 0.06 Hepes buffer Well defined normal valve morphology. Capsule formation nearly absent. Minimal inflammatory cell infiltration.
Treatment: Control —0.06M Hepes buffer Poorly defined valve structure. Massive inflammatory cell infiltration, but little evidence of capsule formation.

EXAMPLE 5

Intact porcine heart valves

Procurement

Porcine heart valves are obtained from isolated hearts immediately following slaughter at an abattoir. The aortic valve and at least one inch or more of ascending aorta is then carefully excised with pre-sterilized instruments.

The valve is washed twice in sterile phosphate buffer solution (PBS) and then placed in sterile, 10° C. PBS for transport. Within three hours of procurement, the valve is brought to the LifeCell facility where it is further trimmed and processed.

Decellularization

After trimming, the intact valve is placed in Decellularization Solution A (DSA). DSA is comprised of 25 mM EDTA, 1M NaCl and 8 mM CHAPS or similar zwitterionic detergent in a sterile PBS base at 7.5 pH. After a 30 minute to one hour incubation, the valve is given two ten minute washes in PBS and then placed in Decellularization Solution B (DSB). DSB is comprised of 25 mM EDTA, 1M NaCl and 1.8 mM Sodium Dodecylsulfate (SDS) or similar anionic or nonionic detergent in a sterile PBS base at 7.5 pH. After a 30 minute to one hour incubation, the valve is given two ten minute washes in PBS.

Vitrification

After decellularization, the valve is placed in Vitrification Solution Fifty-fifty (VSFF) for one to five hours. VSFF is comprised of 2.5% raffinose, 15% polyvinylpyrrolidone (PVP) of 40,000 molecular weight, 15% Dextran of 70,000 molecular weight, and 12% sucrose in a 50/50 (by volume) water-formamide solution. The valve is then rapidly submerged in liquid nitrogen (LN$_2$) until frozen as evidenced by the cessation of boiling. The valve may then be stored in LN$_2$ or LN$_2$ vapor prior to drying.

Drying

After vitrification, the valve is transferred in a nitrogen gas atmosphere to a special Molecular Distillation Dryer sample holder which has been pre-cooled to −196° C. The sample holder is then rapidly transferred under nitrogen gas atmosphere to the Molecular Distillation Dryer. The dryer is then evacuated and a heating cycle initiated which has been optimized specifically for dehydration of VSFF. Under a vacuum less than $1 \times 10^{-6}$ mbar, the sample holder is warmed according to the following protocol:

−196° C.→−150° C. over 10 hours
−150° C.→−70° C. over 80 hours
−70° C.→20° C. over 10 hours The dryer is then opened and the valve transferred to a sealed sterile glass vial under nitrogen gas atmosphere. The valve is then stored at 4° C. until required for transplantation.

Rehydration

Twenty-four hours prior to use, the glass vial is opened in a 100% humidity, 37° C. atmosphere. The valve is allowed to vapor rehydrate in this manner for one to two hours. The valve is then submerged in sterile PBS at 4° C. for two hours. The PBS is then exchanged with fresh solution whereupon the valve is stored at 4° C. overnight. The valve is ready for use the following day.

While the invention has been described in terms of the preferred embodiments, it will be apparent to those of skill in the art that variations and modifications may be applied to the compositions, methods and in the steps or in the sequence of steps of the methods described herein without departing from the concept, spirit and scope of the invention. Such substitutes and modifications are considered to be within the scope of the invention as defined by the appended claims.

What is claimed:

1. A method for processing collagen-based tissue for transplantation comprising:
    (a) procuring said collagen-based tissue and placing said collagen-based tissue into a stabilizing solution to prevent osmotic, hypoxic, autolytic and proteolytic degradation and to protect against microbial contamination;
    (b) incubating said collagen-based tissue in a processing solution to produce processed tissue, said processing solution extracting viable cells from the structural protein and collagen matrix of said collagen-based tissue;
    (c) cryopreparing said processed tissue by incubation in a cryoprotective solution and freezing at cooling rates such that minimal functional damage occurs to the structural protein and collagen matrix of said processed tissue to produce cyoprepared, processed tissue;
    (d) drying said cryoprepared, processed tissue under temperature and pressure conditions that permit removal of water without substantial ice recrystallization or ultrastructural damage, said drying resulting in a residual moisture content of said cyroprepared, processed tissue that permits both storage and rehydration of said tissue, to produce dried, cryoprepared, processed tissue;
    (e) incubating said dried cyroprepared, processed tissue in a rehydration solution, said rehydration solution said rehydration solution preventing osmotic, hypoxic, autolytic, or proteolytic damage, microbial contamination and ultrastructural damage and to result in a rehydrated tissue having a final water content of 20% to 70%; and
    (f) inoculation of said rehydrated tissue with viable cells selected from the group consisting of autogeneic cells, allogeneic cells or combinations thereof or allowing viable cells to repopulate said collagen matrix following transplantation.

2. The method of claim 1 wherein said rehydrated tissue comprises dermis.

3. The method of claim 1 wherein said rehydrated tissue comprises one or more vascular conduits of venous or arterial orgin.

4. The method of claim 1 wherein said rehydrated tissue comprises one or more heart valves.

* * * * *

UNITED STATES PATENT AND TRADEMARK OFFICE
CERTIFICATE OF CORRECTION

PATENT NO. : 5,336,616
DATED : August 9, 1994
INVENTOR(S) : Stephen A. Livesey et al.

It is certified that error appears in the above-identified patent and that said Letters Patent hereby corrected as shown below:

Column 8, line 14, delete "lipoxigenase" and insert therefor --lipoxygenase--;

Column 8, line 57, delete "asmotic" and insert therefor --osmotic--;

Column 8, line 59, delete "pyrolodone" and insert therefor --pyrrolidone--;

Column 10, line 43, delete "(PMSF)" and insert therefor --(PMSF),--;

Column 10, line 44, delete "glycol-bis-(2-aminoethyl(e-" and insert therefor --glycol-bis-(2-aminoethyl e---;

Column 13, line 55, delete "$\mu$/m" and insert therefor --$\mu$m--;

Column 15, line 64, delete "water withdrawing" and insert therefor --water-with-drawing--;

UNITED STATES PATENT AND TRADEMARK OFFICE
CERTIFICATE OF CORRECTION

PATENT NO. : 5,336,616
DATED : August 9, 1994
INVENTOR(S) : Stephen A. Livesey et al.

It is certified that error appears in the above-identified patent and that said Letters Patent hereby corrected as shown below:

Column 19, line 43, delete "E2." and insert therefor --E2,--;

Column 20, line 48, delete "butylrubber" and insert therefor --butyl rubber--;

Column 21, line 59, delete "(gin)", both occurrences, and insert therefor --(gm)--;

Column 23, line 66, delete "Hanks" and insert therefor --Hanks'--;

Column 24, line 13, delete "Hanks" and insert therefor --Hanks'--;

Column 24, line 18, delete "Hanks" and insert therefor --Hanks'--;

Column 24, line 30, delete "Tyvec" and insert therefor --Tyvek--;

Column 24, line 32, delete "Tyvec" and insert therefor --Tyvek--;

UNITED STATES PATENT AND TRADEMARK OFFICE
CERTIFICATE OF CORRECTION

PATENT NO. : 5,336,616
DATED : August 9, 1994
INVENTOR(S) : Stephen A. Livesey et al.

It is certified that error appears in the above-identified patent and that said Letters Patent hereby corrected as shown below:

Column 27, line 5, delete "Hank's" and insert therefor --Hanks'--;

Column 27, line 65, delete "VALE" and insert therefor --VALVE--;

Column 28, line 6, delete "alpha-tocophenol" and insert therefor --alpha-tocopherol--;

Column 28, line 11, delete "pyrrolodone" and insert therefor --pyrrolidone--;

Column 28, line 37, delete "Hepes" and insert therefor --HEPES--;

Column 28, line 38, delete "Hepes" and insert therefor --HEPES--;

Column 28, line 39, delete "Hepes" and insert therefor --HEPES--;

Column 28, line 40, delete "Hepes" and insert therefor --HEPES--;

Column 28, line 62, delete "Hepes" and insert therefor --HEPES--;

Column 28, line 67, delete "Hepes" and insert therefor --HEPES--;

UNITED STATES PATENT AND TRADEMARK OFFICE
CERTIFICATE OF CORRECTION

PATENT NO. : 5,336,616
DATED : August 9, 1994
INVENTOR(S) : Stephen A. Livesey et al.

It is certified that error appears in the above-identified patent and that said Letters Patent hereby corrected as shown below:

Column 29, line 15, delete "Intact porcine heart valves" and insert therefor --INTACT PORCINE HEART VALVES--

Column 30, line 50, delete "said rehydration solution".

Signed and Sealed this

Eleventh Day of July, 1995

Attest:

BRUCE LEHMAN

Attesting Officer          Commissioner of Patents and Trademarks